US007358262B2

(12) United States Patent
Stockwell

(10) Patent No.: US 7,358,262 B2
(45) Date of Patent: Apr. 15, 2008

(54) IDENTIFICATION OF GENOTYPE-SELECTIVE ANTI-TUMOR AGENTS

(75) Inventor: Brent R. Stockwell, New York, NY (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 379 days.

(21) Appl. No.: 10/767,018

(22) Filed: Jan. 29, 2004

(65) Prior Publication Data

US 2004/0248221 A1 Dec. 9, 2004

Related U.S. Application Data

(60) Provisional application No. 60/496,209, filed on Aug. 19, 2003, provisional application No. 60/482,688, filed on Jun. 25, 2003, provisional application No. 60/467,290, filed on May 2, 2003, provisional application No. 60/457,401, filed on Mar. 25, 2003, provisional application No. 60/443,728, filed on Jan. 29, 2003.

(51) Int. Cl.
*A61K 31/02* (2006.01)
*A61K 31/185* (2006.01)
*A61K 31/445* (2006.01)

(52) U.S. Cl. .................. 514/322; 514/576; 514/759
(58) Field of Classification Search ............... None
See application file for complete search history.

(56) References Cited

U.S. PATENT DOCUMENTS

| 6,831,085 | B1 | 12/2004 | Bergnes et al. |
| 2003/0171316 | A1 | 9/2003 | Jupe |
| 2004/0096444 | A1 | 5/2004 | Pizzo et al. |
| 2004/0248221 | A1 | 12/2004 | Stockwell |

FOREIGN PATENT DOCUMENTS

| JP | 07-258224 A | | 10/1995 |
| WO | WO-99/21988 | | 5/1999 |
| WO | WO 01/68641 | * | 9/2001 |
| WO | WO 02/40717 | * | 5/2002 |
| WO | WO-02/083143 | | 10/2002 |
| WO | WO-02/099122 | | 12/2002 |
| WO | WO-2004/030615 | | 4/2004 |
| WO | WO-2004/055519 | | 7/2004 |

OTHER PUBLICATIONS

Stedman's Medical Dictionary, 27th Edition, 2000.*
Dolma et al (Cancer Cell, Mar. 2003, vol. 3, pp. 285-296).*
Ahmed, S. Ansar et al., "A new rapid and simple non-radioactive assay to monitor and determine the proliferation of lymphocytes: an alternative to [³H] thymidine incorporation assay", Journal of Immunological Methods, 170(2): 211-224 (1994) (Abstract).

Aiken, C. T., et al., "A cell-Based Screen for Drugs to Treat Huntington's Disease", Neurobiology of Disease, 16:546-555 (2004).
Andoh, T., et al., "Characterization of a mammalian mutant with a camptothecin-resistant DNA topoisomerase I," Proc Natl Acad Sci U S A, 84:5565-5569 (1987).
Bjornsti, M-A., et al., "Expression of Human DNA Topoisomerase I in Yeast Cells Lacking Yeast DNA Topoisomerase I: Restoration of Sensitivity of the Cells to the Antitumor Drug Camptotchein," Cancer Res , 49:6318-23 (1989).
Bosch, F.X., et al., "The causal relation between human papillomavirus and cervical cancer," J Clin Pathol, 55:244-265 (2002).
Brown, E. J., et al., "A mammalian protein targeted by G1-arresting rapamycin-receptor complex," Nature, 369:756-758 (1994).
Calin, G.A., et al., "Low frequency of alterations of the α (PPP2R1A) and β (PPP2R1B) isoforms of the subunit A of the serine-threonine phosphatase 2A in human neoplasms," Oncogene, 19:1191-1195 (2000).
Capdeville, R., et al., "Glivec (STI571, IMATINIB), A Rationally Developed, Targeted Anticancer Drug," Nat Rev Drug Discov , 1:493-502 (2002).
Champoux, J.J., "Structure-Based Analysis of the Effects of Camptothecin on the Activities of Human Topoisomerase I," Annals New York Acad Sci, 922:56-64 (2000).
Chan, Y-M, et al., "Caspase inhibitors promote the survival of avulsed spinal motoneurons in neonatal rats," NeuroReport, 12(3):541-5 (2001).
D'Arpa, P., et al., "Involvement of Nucleic Acid Synthesis in Cell Killing Mechanisms of Topoisomerase Poisons," Cancer Res, 50:6919-24 (1990).
DeVita, V.T., Jr., et al., "Principles of Cancer Management: Chemotherapy," Cancer: Principles & Practice of Oncology, Fifth Edition, 333-347 (1997).
Dolma, S, et al., "Identification of genotype-selective antitumor agents using synthetic lethal chemical screening in engineered human tumor cells," Cancer Cell, 3:285-296 (2003).
Druker, B.J. et al., "Effects of a selective inhibitor of the Abl tyrosine kinase on the growth of Bcr-Abl positive cells", Nature Medicine, 2:561-566 (1996) (Abstract).
Elenbaas, B. et al., "Human breast cancer cells generated by oncogenic transformation of primary mammary epithelial cells", Genes & Development, 15:50-65 (2001).
Eng, W-K, et al., "Evidence that DNA Topoisomerase I Is Necessary for the Cytotoxic Effects of Camptothecin," Mol Pharmacol, 34:755-60 (1988).
Hahn, W. C. and Weinberg, R. A., "Modelling the Molecular Circuitry of Cancer", Nature Reviews Cancer, 2:331-341 (2002).
Hahn, W.C., et al., "Creation of human tumor cells with defined genetic elements," Nature, 400:464-468 (1999).
Hahn, W.C., et al., "Enumeration of the Simian Virus 40 Early Region Elements Necessary for Human Cell Transformation," Mol Cell Biol, 22(7):2111-23 (2002).

(Continued)

*Primary Examiner*—Karen A. Canella
(74) *Attorney, Agent, or Firm*—Ropes & Gray LLP

(57) ABSTRACT

The present invention relate to methods of identifying a genotype-selective agent. In certain embodiments, the invention relates to agents that are selectively toxic to engineered human tumorigenic cells.

5 Claims, 14 Drawing Sheets

OTHER PUBLICATIONS

Hahn, W.C., et al., "Inhibition of telomerase limits the growth of human cancer cells," Nat Med, 5(10):1164-1170 (1999).

Hamad, N. M. et al., "Distinct requirements for Ras oncogenesis in human versus mouse cells", Genes & Development, 16:2045-2057 (2002).

Harley, C.B., "Telomerases," *Pathol Biol* (Paris), 42:342-5 (1994).

Hsiang, Y-H. and Liu, L.F., "Identification of Mammalian DNA Topoisomerase I as an Intracellular Target of the Anticancer Drug Camptothecin," *Cancer Res*, 48:1722-6 (1988).

Hsiang, Y-H., et al., "Arrest of Replication Forks by Drug-stabilized Topoisomerase I-DNA Cleavable Complexes as a Mechanism of Cell Killing by Camptothecin," *Cancer Res*, 49:5077-82 (1989).

Jorcyk, C.L., et al., "Development and Characterization of a Mouse Prostate Adenocarcinoma Cell Line: Ductal Formation Determined by Extracellular Matrix," The Prostate, 34:10-22 (1998).

Kohno, T., et al., "Alterations of the *PPP1R3* Gene in Human Cancer," *Cancer Res*, 59:4170-4 (1999).

Laurent, G. and Jaffrezou, J-P., "Signaling pathways activated by daunorubicin," Blood, 98(4):913-924 (2001).

Lessnick, S.L., et al., "The Ewing's sarcoma oncoprotein EWS/FLI induces a p53- dependent growth arrest in primary human fibroblasts," Cancer Cell, 1:393-401 (2002).

Liu, L.F., et al., "Mechanism of Action of Camptothecin," Annals N Y Acad Sci, 922:1-10 (2000).

Loomis, C.R. and Bell, R.M., "Sangivamycin, a Nucleoside Analogue, Is a Potent Inhibitor of Protein Kinase C★," J Biol Chem, 263(4):1682-1692 (1998).

Madden, K.R., and Champoux, J.J., "Overexpression of Human Topoisomerase I in Baby Hamster Kidney Cells: Hypersensitivity of Clonal Isolates to Camptothecin," *Cancer Res*, 52:525-32 (1992).

Majno, G. and Joris, I., "Apoptosis, Oncosis, and Necrosis," *Am J Pathol*, 146(1):3-15 (1995).

Makin, G., "Targeting apoptosis in cancer chemotherapy," *Expert Opin Ther Targets*, 6(1):73-84 (2002).

Miller, M.L. and Ojima, I., "Chemistry and Chemical Biology of Taxane Anticancer Agents," Chem. Record, 1:195-211 (2001).

Millward, T.A., et al., "Regulation of protein kinase cascades by protein phosphatase 2A," Trends Biochem Sci, 24:186-91 (1999).

Mokbel, K. and Hassanally, D., "From HER2 to Herceptin," *Curr Med Res Opin*, 17(1):51-9 (2001).

Müler, I., et al:, Anthracycline-derived chemotherapeutics in apoptosis and free radical cytotoxicity (Review), *Int J Mol Med*, 1:491-4 (1998).

Nociari, M.M., et al., "A novel one-step, highly sensitive fluorometric assay to evaluate cell-mediated cytotoxicity," *J. Immunol. Methods*, 213:157-167 (1998).

Pallas, D.C., et al., "Polyoma small and middle T antigens and SV40 small t antigen form stable complexes with protein phosphatase 2A," Cell, 60:167-176 (1990).

Perez-Stable, C., et al., "Prostate Cancer Progression, Metastasis, and Gene Expression in Transgenic Mice," *Cancer Res*, 57:900-6 (1997).

Rao, K.V., "Structure of Sangivamycin," *J Med Chem*, 11:939-41 (1969).

Rich, J.N., et al., "A Genetically Tractable Model of Human Glioma Formation," *Cancer Res*, 61:3556-60 (2001).

Richard, D., et al., "Free radical production and labile Iron pool decrease triggered by subtoxic concentration of aclarubicin in human leukemia cell lines," Leukemia Res, 26:927-931 (2002).

Ruediger, R., et al., "Alterations in protein phosphatase 2A subunit interaction in human carcinomas of the lung and colon with mutations in the Aβ subunit gene," Oncogene, 20:1892-1899 (2001).

Ruediger, R., et al., "Disruption of protein phosphatase 2A subunit Interaction in human cancers with mutations in the Aα subunit gene," Oncogene, 20:10-15 (2001).

Sabatini, D.M., et al., "RAFT1: A mammalian protein that binds to FKBP12 in a rapamycin-dependent fashion and is homologous to yeast TORs," Cell, 78:35-43 (1994).

Sandmoller, A., et al., "A Transgenic Mouse Model for Lung Adenocarcinoma," *Cell Growth & Differ*, 6:97-103 (1995).

Schreiber, S.L., Chemical Genetics Resulting from a Passion for Synthetic Organic Chemistry, Bioorg. Med. Chem., 6:1127-1152 (1998).

Sellers, W.R. and Kaelin, W.G., "Role of the retinoblastoma protein in the pathogenesis of human cancer," J Clin Oncol, 15:3301-3312 (1997).

Shawver, L.K., et al., "Smart drugs: Tyrosine kinase inhibitors in cancer therapy," Cancer Cell, 1:117-123 (2002).

Sherr, C.J., "The *INK4a|ARF* Network in Tumour Suppression," Nat Rev Mol Cell Biol, 2:731-737 (2001).

Shi, Y., et al., "Enhanced Sensitivity of Multiple Myeloma Cells Containing *PTEN* Mutations to CCI-779," *Cancer Res*, 62:5027-34 (2002).

Simons, A., et al., "Establishment of Chemical Synthetic Lethality Screen in Cultured Human Cells," Genome Res, 11:266-273 (2001).

Stockwell, B. R., "Chemical Genetic Screening Approaches to Neurobiology," Neuron, 36:559-562 (2002).

Stockwell, B. R., "Frontiers in chemical genetics", Trends Biotechnol 18, 449-55, (2000).

Stockwell, B.R., Chemical Genetics: Ligand-Based Discovery of Gene Function, Nat Rev Genet, 1:116-125 (2000).

Stockwell, B.R., "The biological magic behind the bullets," Nature Biotechnology, 22(1):37-38 (2004).

Stockwell, B.R., et al., "High-throughput screening of small molecules in miniaturized mammalian cell-based assays involving post-translational modifications," Chem Biol, 6:71-83 (1999).

Testa, J.R. and Giordano, A., "SV40 and cell cycle perturbations in malignant mesothelioma," Seminars In Cancer Biol, 11:31-8 (2001).

Torrance, C.J., et al., "Use of isogenic human cancer cells for high-throughput screening and drug discovery," Nat Biotechnol, 19:940-945 (2001).

Traganos, F., et al., "Induction of Apoptosis by Camptothecin and Topotecan," *Ann N Y Acad Sci*, 803:101-10 (1996).

Tsao, Y-P., et al., "Interaction between Replication Forks and Topoisomerase I-DNA Cleavable Complexes: Studies in a Cell-free SV40 DNA Replication System," *Cancer Res*, 53:5908-14 (1993).

Van Dyke, M, M. and Dervan, Peter B., "Echinomycin Binding Sites on DNA", Science 225:1122-1127 (1984).

Vonsattel J.P.G., "Neuropathology of Huntington's Disease," *Neuroscience News*, 3(2-3):45-53 (2000).

Wang, S.S., et al., "Alterations of the *PPP2R1B* Gene in Human Lung and Colon Cancer," Science, 282:284-287 (1998).

Wang, X. M. et al., "A new microcellular cytotoxicity test based on calcein AM release", Human Immunology, 37(4):264-270 (1993) (Abstract).

Waring, M.J. and Wakelin, L.P.G., "Echinormycin: a bifunctional intercalating antibiotic," Nature, 252:653-7 (1974).

Weinstein, J.N., et al, "An Information-Intensive Approach to the Molecular Pharmacology of Cancer," Science, 275:343-349 (1997).

Zalacain, M., et al., "The mode of action of the antitumor drug bouvardin, an inhibitor of protein synthesis in eukaryotic cells," FEBS Lett, 148(1):95-97 (1982).

Abdel-Alim, et al., "Synthesis and biological activities of 6-bromo-2,3-disubstituted-4-(3H)-quinazolinones," Indian Journal of Chemistry, 33(B):260-265 (1994).

Adam, et al., "Comprehensive Proteomic Analysis of Breast Cancer Cell Membranes Reveals Unique Proteins with Potential Roles in Clinical Cancer," JBC Papers in Press, 1-60 (2002).

Ager, et al., "Synthesis and Central Nervous System Activity of Quinazolones Related to 2-Methyl-3-(o-tolyl)-4(3H)-quinazolone (Methaqualone)," J. Med. Chem. 20(3):379-386 (1977).

Database Registry Chemical Abstracts Service, Columbus, Ohio, US; (May 21, 2001), XP002405284, RN 336853-04-4.

Database Registry Chemical Abstracts Service, Columbus, Ohio, US; (May 21, 2001), XP002405285, RN 336813-90-2.

Dolma, et al., "Identification of genotype-selective antitumor agents using synthetic lethal chemical screening in engineered human tumor cells," Cancer Cell, 3:285-296 (2003).

Figys, et al., "VDAC Can Control Apoptosis By Controlling Metabolism," Biophysical, Jr., 86(1):463A-464A (2004).

Gupta, et al., "A Novel Class of Hypoglycaemic Agents: Syntheses & SAR in 2-Substituted 4(3H)-Quinazolones, 2-Substituted 4-Hydroxypolymethylene[5,6]pyrimidines & 3-Substituted 4-Oxo-pyrido[1,2-α]pyrimidines," Indian Journal of Chemistry, 9:201-206 (1971).

Ikonen, et al., "Prohibitin, an antiproliferative protein, is localized to mitochondria," FEBS Letters, 358(3):273-277 (1995).

Kozhevnikov, et al., "Synthesis in the 2-aminoethyl-3-(2'-tolyl)-4-quinazolone," Khimiko-Farmatsevticheskii Zhurnal, 4(11):22-25 (1970).

Tani, et al., "Studies on Biologically Active Halogenated Compounds II. Chemical Modifications of 6-amino-2-fluoromethyl-3-(o-toly)-4(3H) quinazolinone and the CNS depressant activities of related compounds," Chemical and Pharmaceutical Bulletin, Pharmaceutical Society of Japan, 27(11):2675-2687 (1979).

Verma, et al., "A New Potent Anti-Inflammatory Quinazolone," Pharmacological Research Communications, Italian Pharmacological Society, IT, 13(10):967-979 (1981).

* cited by examiner

Structure Activity Relationship for Erastin

- Tested 135 analogs of erastin for activity and selectivity (tumor vs. normal)
- 134 were inactive
- 1 was active and selective, but less potent than erastin Figure 14. Dose-Response for Suppressor of Mutant Huntingtin-Induced Toxicity

IDENTIFICATION OF GENOTYPE-SELECTIVE ANTI-TUMOR AGENTS

RELATED APPLICATIONS

This application claims the benefit of priority of U.S. Provisional Application No. 60/496,209, filed Aug. 19, 2003; U.S. Provisional Application No. 60/482,688, filed Jun. 25, 2003; U.S. Provisional Application No. 60/467,290, filed May 2, 2003; U.S. Provisional Application No. 60/457,401, filed Mar. 25, 2003; and U.S. Provisional Application No. 60/443,728, filed Jan. 29, 2003. The entire teachings of the referenced Provisional Applications are incorporated herein by reference in their entirety.

FUNDING

Work described herein was funded, in whole or in part, by National Cancer Institute Grant 1R01CA97061-01. The United States government has certain rights in the invention.

BACKGROUND OF THE INVENTION

Many drugs administered to treat a disease are targeted against general differences between a diseased cell and a normal cell. For example, paclitaxel, which is used to treat ovarian and breast cancer and inhibits microtubule function, is thought to exhibit tumor cell specificity based on the greater rate of proliferation of tumor cells relative to normal cells (Miller and Ojima, Chem. Rec., 1:195-211 (2002)). However, despite this consensus view, paclitaxel's in vitro activity varies widely across tumor cell lines (Weinstein et al, Science 275:343-349 (1997)), indicating that genetic factors can modify sensitivity of tumor cells to paclitaxel and that the responsiveness of tumor cells is not simply determined by their rate of proliferation.

Molecularly targeted therapeutics represent a promising new approach to anti-cancer drug discovery (Shawver et al., 2002, Cancer Cell 1, 117-23). Using this approach, small molecules are designed to inhibit directly the very oncogenic proteins that are mutated or overexpressed in specific tumor cell types. By targeting specific molecular defects found within tumor cells, this approach may ultimately yield therapies tailored to each tumor's genetic makeup. Two recent examples of successful molecularly targeted anti-cancer therapeutics are Gleevec (imatinib mesylate), an inhibitor of the breakpoint cluster region-abelsen kinase (BCR-ABL) oncoprotein found in Philadelphia chromosome-positive chronic myelogenous leukemia (Capdeville et al., 2002, Nat Rev Drug Discov 1, 493-502) and Herceptin (trastuzumab), a monoclonal antibody targeted against the HER2/NEU oncoprotein found in metastatic breast cancers (Mokbel and Hassanally, 2001, Curr Med Res Opin 17, 51-9).

A complementary strategy involves searching for genotype-selective anti-tumor agents that become lethal to tumor cells only in the presence of specific oncoproteins or in the absence of specific tumor suppressors. Such genotype-selective compounds might target oncoproteins directly or they might target other critical proteins involved in oncoprotein-linked signaling networks. Compounds that have been reported to display synthetic lethality include (i) the rapamycin analog CCI-779 in myeloma cells lacking PTEN (Shi et al., 2002, Cancer Res 62, 5027-34), (ii) Gleevec in BCR-ABL-transformed cells (Druker et al., 1996, Nat Med 2, 561-6) and (iii) a variety of less well-characterized compounds (Stockwell et al., 1999, Chem Biol 6, 71-83; Torrance et al., 2001, Nat Biotechnol 19, 940-5).

SUMMARY OF THE INVENTION

Described herein is a synthetic lethal screening method, particularly a synthetic lethal high-throughout screening method, useful to identify agents or drugs for treating or preventing conditions or diseases such as the presence or development of tumors or other conditions characterized by hyperproliferation of cells (e.g., leukemia). An agent or drug identified by such a method can be used to treat or prevent cancer (e.g., tumors or leukemia) in an individual, such as a human in need of treatment or prevention.

Also described herein is a genotype-selective method for identifying drugs or agents for treating or preventing Huntington's disease (HD). As used herein, the terms "agent" and "drug" are used interchangeability; they can be compounds or molecules.

In one aspect, the present invention relates to screening methods for identifying compounds that kill or inhibit the growth of tumorigenic cells, such as engineered tumorigenic cells, but not their isogenic normal cell counterparts. The method has been used to identify known and novel compounds with genotype-selective activity, including the known compounds doxorubicin, daunorubicin, mitoxantrone, camptothecin, sangivamycin, echinomycin, bouvardin, NSC146109 and a novel compound referred to herein as erastin. These compounds have increased activity in the presence of one or more of the following: hTERT oncoprotein, the SV40 large T oncoprotein, small T oncoprotein, human papillomavirus type 16 (HPV) E6 oncoprotein, HPV E7 oncoprotein, and oncogenic HRAS. Applicants determined that over-expression of hTERT and either E7 or LT increased expression of topoisomerase $2\alpha$ and that overexpressing $RAS^{V12}$ and ST in cells expressing hTERT both increased expression of topoisomerase 1 and sensitized cells to a non-apoptotic cell death process initiated by erastin.

The invention relates to a method of identifying agents (drugs) that are selectively toxic to (e.g., kill or inhibit the growth of) tumorigenic cells, such as engineered tumorigenic cells, including human tumorigenic cells (e.g., engineered human tumorigenic cells). In one embodiment, the invention relates to a method of identifying an agent (drug) that selectively kills or inhibits the growth of (is toxic to) engineered human tumorigenic cells, comprising contacting test cells, which are engineered human tumorigenic cells, with a candidate agent; determining viability of test cells contacted with the candidate agent; and comparing the viability of the test cells with the viability of an appropriate control. In all embodiments, viability is assessed by determining the ability of an agent (drug) to kill cells or inhibit growth/proliferation of cells, or both. If the viability of the test cells is less than that of the control cells, then an agent (drug) that is selectively toxic to (kills or inhibits the growth of) engineered human tumorigenic cells is identified. An appropriate control is a cell that is the same type of cell as the test cell, except that the control cell is not engineered to be tumorigenic. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference).

In one embodiment, the method of identifying an agent selectively toxic to tumorigenic cells comprises further assessing the toxicity of an agent identified as a result of screening in engineered human tumorigenic cells in an appropriate animal model or in an additional cell-based or non cell-based system or assay. For example, an agent or drug so identified can be assessed for its toxicity to cancer cells such as tumor cells or leukemia cells obtained from individuals or its toxicity to a (one or more) cancer (tumor) cell line. For example, the method can comprise further assessing the selective toxicity of an agent (drug) to tumorigenic cells in an appropriate mouse model or nonhuman primate. The invention further relates to a method of producing an agent (drug) that is identified by the method of the present invention such as an agent (drug) that is selectively toxic to engineered human tumorigenic cells. An agent (drug) that is shown to be selectively toxic to tumorigenic cells is synthesized using known methods.

The invention additionally relates to a method of identifying agents (drugs) that are toxic to engineered tumorigenic cells, such as engineered human tumorigenic cells. In one embodiment, the invention relates to a method of identifying an agent (drug) that kills or inhibits the growth of (is toxic to) engineered human tumorigenic cells, comprising contacting test cells, which are engineered human tumorigenic cells, with a candidate agent; determining viability of the test cells contacted with the candidate agent; and comparing the viability of the test cells with the viability of an appropriate control. If the viability of the test cells is less than that of the control cells, then an agent (drug) that is toxic to (kills or inhibits the growth of) engineered human tumorigenic cells is identified. Here, an appropriate control is a cell that is the same type of cell (engineered human tumorigenic cell) as the test cells, except that the control cell is not contacted with the candidate agent. An appropriate control may be run simultaneously, or it may be pre-established (e.g., a pre-established standard or reference). For example, an agent or drug so identified can be assessed for its toxicity to cancer cells such as tumor cells or leukemia cells obtained from individuals or its toxicity to a (one or more) cancer (tumor) cell line.

In one embodiment, the method of identifying an agent toxic to engineered tumorigenic cells comprises further assessing the toxicity of an agent identified as a result of screening in engineered human tumorigenic cells in an appropriate animal model or in an additional cell-based or non cell-based system or assay. For example, the method can comprise further assessing the toxicity of an agent (drug) to tumorigenic cells in an appropriate mouse model or nonhuman primate. The invention further relates to a method of producing an agent (drug) that is identified by the method of the present invention, such as an agent (drug) that is toxic to engineered human tumorigenic cells. An agent (drug) that is shown to be toxic to tumorigenic cells is synthesized using known methods.

In certain embodiments of the invention, a candidate agent is identified by screening an annotated compound library, a combinatorial library, or other library which comprises unknown or known compounds (agents, drugs) or both.

In certain embodiments, the invention relates to the compound, erastin. In additional embodiments, the invention relates to the compound, erastin B. In further embodiments of the invention, the invention relates to analogs of erastin that selectively kill or inhibit the growth of (are toxic to) engineered human tumorigenic cells. Optionally, the compound of the invention is formulated with a pharmaceutically acceptable carrier.

The invention further relates to methods of identifying cellular components involved in tumorigenesis. Cellular components include, for example, proteins (e.g., enzymes, receptors), nucleic acids (e.g., DNA, RNA), and lipids (e.g., phospholipids). In one embodiment, the invention relates to a method of identifying a (one or more) cellular component involved in tumorigenesis wherein (a) a cell, such as an engineered human tumorigenic cell, is contacted with erastin; and (b) a cellular component that interacts with erastin, either directly or indirectly, is identified. The cellular component that is identified is a cellular component involved in tumorigenesis. In an additional embodiment, the invention relates to a method of identifying a (one or more) cellular component that interacts with erastin wherein (a) a cell, such as an engineered human tumorigenic cell, is contacted with erastin; and (b) a cellular component that interacts with erastin, either directly or indirectly, is identified. The cellular component that is identified is a cellular component that interacts with erastin.

The invention additionally relates to methods of treating or preventing cancer. In one embodiment, the invention relates to a method of treating or preventing cancer in which a therapeutically effective amount of a compound, such as, for example, erastin, is administered to an individual in need of treatment of cancer. In certain embodiments, the cancer is characterized by cells in which the RAS pathway is activated. In certain further embodiments, the cancer is characterized by cells expressing SV40 small T oncoprotein and/or oncogenic HRAS.

The invention also relates to methods of identifying agents (drugs) that interact with a (one or more) cellular component that interacts, directly or indirectly, with erastin. In one embodiment, the invention relates to a method of identifying an agent that interacts with a cellular component that interacts with erastin, comprising (a) contacting a cell with erastin; (b) identifying a cellular component that interacts (directly or indirectly) with erastin; (c) contacting a cell with a candidate agent, which is an agent or drug to be assessed or its ability to interact with cellular component(s) that interacts with erastin; and (d) determining whether the agent that interacts (directly or indirectly) with the cellular component in (b). If the agent interacts with the cellular component in (b), it is an agent that interacts with a cellular component that interacts with erastin. In certain embodiments, the cell is an engineered human tumorigenic cell. In further embodiments, the invention relates to compounds that interact, directly or indirectly, with a (one or more) cellular component that interacts with erastin. In certain embodiments, the cellular component that interacts with erastin is involved in tumorigenesis. An agent (drug) that is shown to interact with a cellular component that interacts with erastin is synthesized using known methods.

The invention further relates to a method of identifying an agent (drug) that induces death in tumor cells by a non-apoptotic mechanism. In one embodiment, a method of identifying an agent that induces death in tumor cells by a non-apoptotic mechanism comprises (a) contacting test cells, which are tumor cells, with a candidate agent that induces death in tumor cells; (b) assessing whether the agent in (a) induces apoptosis in test cells; and (c) comparing induction of apoptosis in cells in (b) with an appropriate control. If apoptosis is induced in the control cells but not in test cells, then an agent (drug) that induces death in tumor cells by a non-apoptotic mechanism is identified. An appropriate control is a cell that is the same type of cell as that of test cells except that the control cell is contacted with an agent known to induce apoptosis in the cell. An appropriate control may be run simultaneously, or it may be pre-established (e.g., a pre-established standard or reference). In certain embodiments, the test cells are engineered human tumorigenic cells.

In certain aspects, the present invention provides methods of conducting a drug discovery business. In one embodiment, the invention relates to a method of conducting a drug discovery business, comprising: (a) identifying an (one or more) agent (drug) that is selectively toxic to engineered human tumorigenic cells; (b) assessing the efficacy and toxicity of an agent identified in (a), or analogs thereof, in animals; and (c) formulating a pharmaceutical preparation including one or more agents assessed in (b). For example, the agent identified is erastin. The efficacy assessed may be the ability of an agent to selectively induce cell death in tumorigenic cells in an animal. In a further embodiment, the method of conducting a drug discovery business comprises establishing a distribution system for distributing the pharmaceutical preparation for sale. Optionally, a sales group is established for marketing the pharmaceutical preparation. In an additional embodiment, the invention relates to a method of conducting a proteomics business, comprising identifying an agent (drug) that is selectively toxic to engineered human tumorigenic cells and licensing, to a third party, the rights for further drug development of agents that is selectively toxic to engineered human tumorigenic cells.

In another embodiment, the invention relates to a method of conducting a drug discovery business, comprising: (a) identifying an (one or more) agent (drug) that is toxic to engineered human tumorigenic cells; (b) assessing the efficacy and toxicity of an agent identified in (a), or analogs thereof, in animals; and (c) formulating a pharmaceutical preparation including one or more agents assessed in (b). For example, the agent identified is erastin. The efficacy assessed may be the ability of an agent to selectively induce cell death in tumorigenic cells in an animal. In a further embodiment, the method of conducting a drug discovery business comprises establishing a distribution system for distributing the pharmaceutical preparation for sale. Optionally, a sales group is established for marketing the pharmaceutical preparation. In an additional embodiment, the invention relates to a method of conducting a proteomics business, comprising identifying an agent (drug) that is toxic to engineered human tumorigenic cells and licensing, to a third party, the rights for further drug development of agents that is toxic to engineered human tumorigenic cells.

In a further embodiment, the invention relates to a method of conducting a drug discovery business, comprising: (a) identifying an (one or more) agent (drug) that interacts with a cellular component that interacts with erastin; (b) assessing the efficacy and toxicity of an agent identified in (a), or analogs thereof, in animals; and (c) formulating a pharmaceutical preparation including one or more agents assessed in (b). The efficacy assessed of an agent may be its ability to selectively induce cell death in tumorigenic cells in an animal. In a further embodiment, the method of conducting a drug discovery business comprises establishing a distribution system for distributing the pharmaceutical preparation for sale. Optionally, a sales group is established for marketing the pharmaceutical preparation. In an additional embodiment, the invention relates to a method of conducting a proteomics business, comprising identifying an agent (drug) that interacts with a cellular component that interacts with erastin and licensing, to a third party, the rights for further drug development of agents that interact with a cellular component that interacts with erastin.

Identifying genetic alterations that increase the sensitivity of human cells to specific compounds may ultimately allow for mechanistic dissection of oncogenic signaling networks and tailoring chemotherapy to specific tumor types. Applicants have developed a systematic process for discovering small molecules with increased activity in cells harboring specific genetic changes. Using this system, they determined that several clinically used anti-tumor agents are more potent and more active in the presence of specific genetic elements. Moreover, they identified a novel compound that selectively kills cells expressing the Small T oncoprotein and oncogenic RAS. These genetically-targeted small molecules may also serve as leads for development of anti-cancer drugs with a favorable therapeutic index.

The present invention further provides packaged pharmaceuticals. In one embodiment, the packaged pharmaceutical comprises: (i) a therapeutically effective amount of an agent that is selectively toxic to engineered human tumorigenic cells; and (ii) instructions and/or a label for administration of the agent for the treatment of patients having cancer. For example, the agent is erastin. In another embodiment, the packaged pharmaceutical comprises: (i) a therapeutically effective amount of an agent that is toxic to engineered human tumorigenic cells; and (ii) instructions and/or a label for administration of the agent for the treatment of patients having cancer. In another related embodiment, the packaged pharmaceutical comprises: (i) a therapeutically effective amount of an agent that that interacts with a cellular component that interacts with erastin; and (ii) instructions and/or a label for administration of the agent for the treatment of patients having cancer.

The present invention further provides use of any agent identified by the present invention in the manufacture of medicament for the treatment of cancer, for example, use of erastin or its analogs in the manufacture of medicament for the treatment of cancer.

In another aspect, the present invention relates to screening methods for identifying compounds that suppress cellular toxicity of a protein, such as a mutant huntingtin protein, in engineered cells (such as engineered neuronal cells expressing a mutant huntingtin protein), but not their isogenic normal cell counterparts. These methods have been used to identify known and novel compounds with genotype-selective activity, including tubulin inhibitors. Optionally, these compounds have increased activity in the presence of a mutant huntingtin protein.

The invention relates to a method of identifying agents (drugs) that selectively suppresses the cellular toxicity in engineered cells, for example, engineered neuronal cells expressing a mutant huntingtin protein. In one embodiment, the invention relates to a method of identifying an agent (drug) that suppresses the cellular toxicity of a mutant huntingtin protein in engineered cells, comprising contacting test cells (e.g., engineered neuronal cells expressing a mutant huntingtin protein) with a candidate agent; determining viability of the test cells contacted with the candidate agent; and comparing the viability of the test cells with the viability of an appropriate control. If the viability of the test cells is more than that of the control cells, then an agent (drug) that selectively suppresses the cellular toxicity (e.g., huntingtin-induced cellular toxicity) is identified. An appropriate control is a cell that is the same type of cell as that of test cells except that the control cell is not engineered to express a protein which causes toxicity. For example, control cells may be the parental primary cells from which the test cells are derived. Control cells are contacted with the candidate agent under the same conditions as the test cells.

An appropriate control may be run simultaneously, or it may be pre-established (e.g., a pre-established standard or reference).

In certain embodiments, the present invention relates to a method of treating or preventing a neurodegenerative disorder associated with polyglutamine (polyQ) expansion in an individual comprising administering to the individual a therapeutically effective amount of a compound identified by the methods, such as a tubulin inhibitor (e.g., a tubulin inhibitor shown in FIG. 15). Examples of the neurodegenerative disorders associated with polyQ expansion include, but are not limited to, Huntington's disease, spinobulbar muscular atrophy, dentatorubral pallidoluysian atrophy, and the spinocerebellar ataxias type 1, 2, 3, 6, 7, and 17.

BRIEF DESCRIPTION OF THE DRAWINGS

FIG. 15 shows the tubulin inhibitors that suppressed mutant Huntingtin-induced cell death.

DETAILED DESCRIPTION OF THE INVENTION

The ability of genotype-selective compounds to serve as molecular probes is based on the premise of chemical genetics—that small molecules can be used to identify proteins and pathways underlying biological effects (Schreiber, 1998, Bioorg. Med. Chem. 6, 1127-1152; Stockwell, 2000, Nat Rev Genet 1, 116-25; Stockwell, 2000, Trends Biotechnol 18, 449-55). For example, the observation that the natural product rapamycin retards cell growth made possible the discovery of the mammalian Target of Rapamycin (mTOR) as a protein that regulates cell growth (Brown et al., 1994, Nature 369, 756-758; Sabatini et al., 1994, Cell 78, 35-43). Applicants have combined these two approaches, chemical and molecular genetic, to discover pathways affected by mutations associated with human diseases such as cancer and HD.

Over the past several years, Applicants and others have engineered a series of human tumor cells with defined genetic elements in order to identify those critical pathways whose disruption leads to a tumorigenic phenotype (Hahn et al., 1999, Nat Med 5, 1164-70; Hahn et al., 2002, Nat Rev Cancer 2, 331-41; Lessnick et al., 2002, Cancer Cell 1, 393-401). Applicants postulated that these experimentally transformed cells would make it possible to identify genotype-selective agents from both known and novel compound sources that exhibit synthetic lethality in the presence of specific cancer-related alleles. Compounds with genotype-selective lethality may serve as molecular probes of signaling networks present in tumor cells and as leads for subsequent development of clinically effective drugs with a favorable therapeutic index.

Similarly, Applicants have developed high-throughput screens for suppressors (e.g., small molecules) of the toxicity of expanded huntingtin (eHtt) in neuronal cells. Applicants have screened a collection of compounds in these assays and identified compounds that promote viability of neuronal cells expressing mutant huntingtin, but not of neuronal cells lacking mutant huntingtin. These identified genotype-selective compounds may serve as molecular probes of signaling networks present in neuronal cells from HD patients, and as leads for subsequent development of clinically effective drugs with a favorable therapeutic index.

Engineered Cell Lines

In one aspect, the present invention relates to engineered tumorigenic cell lines.

Figure 1:
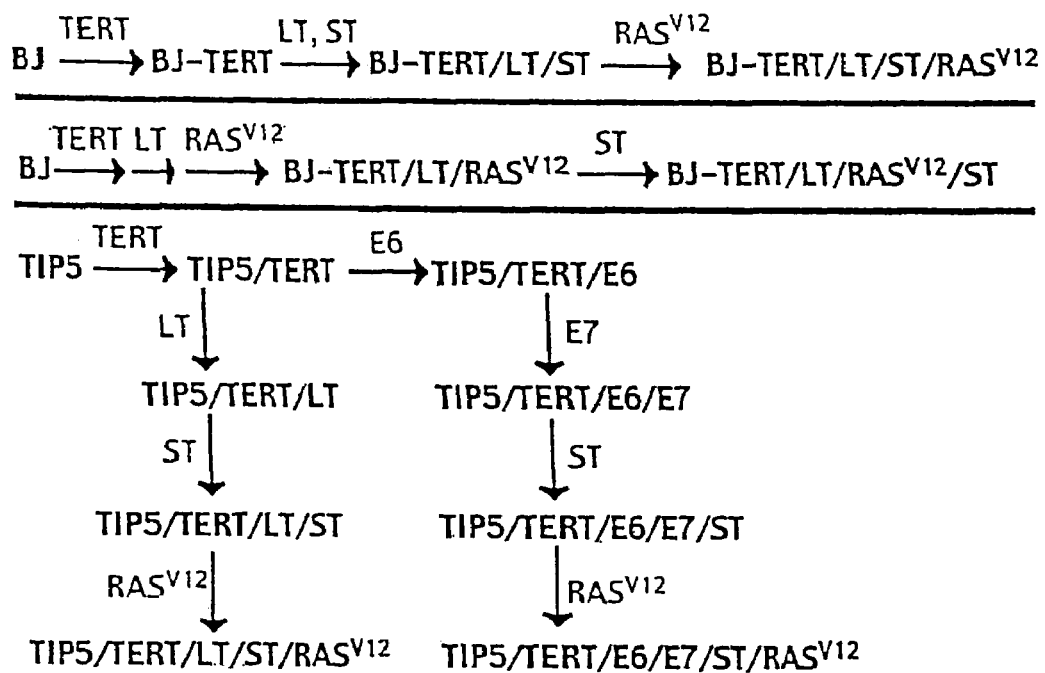
FIG. 1 is a schematic showing the relationships among experimentally transformed human cells. BJ cells are primary human foreskin fibroblasts. BJ-TERT cells are derived from BJ cells and express hTERT, the catalytic subunit of the enzyme telomerase. BJ-TERT/LT/ST cells are derived from BJ-TERT cells by introduction of a genomic construct encoding both simian virus 40 large (LT) and small T (ST) oncoproteins. BJ-TERT/LT/ST/RAS$^{V12}$ tumor cells are derived from BJ-TERT/LT/ST cells by introduction of an oncogenic allele of HRAS (RAS$^{V12}$) (Hahn et al., 1999, Nat Med 5, 1164-70). BJ-TERT/LT/RAS$^{V12}$ cells are derived from BJ cells by introduction of cDNA constructs encoding TERT, LT, RAS$^{V12}$ and a control vector (Hahn et al., 2002, Nat Rev Cancer 2, 331-41). BJ-TERT/LT/RAS$^{V12}$/ST cells are derived from BJ-TERT/LT/RAS$^{V12}$ cells by introduction of a cDNA encoding ST (Hahn et al., 2002, Nat Rev Cancer 2, 331-41). TIP5 cells are primary human foreskin fibroblasts. The TIP5-derived cell lines were prepared by introducing vectors encoding hTERT, LT, ST, RAS, or the papillomavirus E6 or E7 proteins, as shown. E6 and E7 can jointly substitute for LT (Lessnick et al., 2002, Cancer Cell 1, 393-401).

Previous reports have indicated that it is possible to convert primary human cells into tumorigenic cells by introduction of vectors expressing the hTERT and oncogenic RAS proteins as well as others that disrupt the function of p53, RB and PP2A (Hahn et al., 2002, Mol Cell Biol 22, 2111-23; Hahn et al., 1999, Nature 400, 464-8; Hahn and Weinberg, 2002, Nat Rev Cancer 2, 331-41; Lessnick et al., 2002, Cancer Cell 1, 393-401). Applicants made use of a series of engineered human tumorigenic cells and their precursors, which were created by introducing specific genetic elements into primary human foreskin fibroblasts (FIG. 1). A variety of characteristics of these engineered tumorigenic cells have been reported previously, including their doubling time, their resistance to replicative senescence and crisis in culture, their response to gamma irradiation, their ability to grow in an anchorage-independent fashion and their ability to form tumors in immunodeficient mice (Hahn et al., 1999, supra; Hahn et al., 2002, supra; Lessnick et al., 2002, supra).

In one series of engineered cells, the following genetic elements were introduced sequentially into primary BJ fibroblasts: the human catalytic subunit of the enzyme telomerase (hTERT), a genomic construct encoding the Simian Virus 40 large (LT) and small T (ST) oncoproteins, and an oncogenic allele of HRAS (RAS$^{V12}$). The resulting transformed cell lines were named, respectively: BJ-TERT, BJ-TERT/LT/ST, and BJ-TERT/LT/ST/RAS$^{V12}$. In a second series, cell lines were created in which complementary DNA (cDNA) constructs encoding LT and ST were used in place of the SV40 genomic construct that encodes both of these viral proteins. In this latter series, ST was introduced in the last stage, enabling Applicants to test compounds in the presence or absence of ST. This latter engineered human tumorigenic cell line was named BJ-TERT/LT/RAS$^{V12}$/ST.

In a third series, cell lines derived from independently prepared human TIP5 foreskin fibroblasts created by introducing cDNA constructs encoding hTERT, LT, ST and RAS$^{V12}$ (Lessnick et al., 2002, Cancer Cell 1, 393-401) were used. These cell lines were called, respectively: TIP5/TERT, TIP5/TERT/LT, TIP5/TERT/LT/ST, and TIP5/TERT/LT/ST/RAS$^{V12}$. In a fourth series, cell lines derived from TIP5 fibroblasts created by introducing cDNA constructs encoding hTERT, E6, E7, ST and RAS$^{V12}$ were used. These cell lines were named, respectively: TIP5/TERT/E6, TIP5/TERT/E6/E7, TIP5/TERT/E6/E7/ST, and TIP5/TERT/E6/E7/ST/RAS$^{V12}$. In this series, HPV E6 and E7, which inactivate p53 and RB, respectively, serve a similar function as LT in the previous series. However, by using HPV E6 and E7, Applicants were able to observe the effects of inactivating, separately and independently, p53 and RB. Results of a large-scale screen for compounds that display selective killing of these engineered tumorigenic cell lines are described in the examples that follow.

In another embodiment, the present invention relates to engineered neuronal cell lines, for example, neuronal cells engineered to express a mutant huntingtin protein. Non-limiting examples of these neuronal cells include PC12 cells and ST14A cells as described in the invention. To illustrate, PC12 cells or ST14A cells can be transfected with exon-1 of the human huntingtin gene containing 103 N-terminal polyQ repeats (Q103).

Methods of Screening for Genotype-Selective Compounds

In certain embodiments, the invention relates to large-scale screens for compounds that display selective killing of or inhibiting the growth of (are selectively toxic to) engineered tumorigenic cell lines. As used herein, the terms agent and drug are used interchangeably. As used herein, the term "is toxic to" refers to the ability of an agent or compound to kill or inhibit the growth/proliferation of tumorigenic cells. Large-scale screens include screens wherein hundreds or thousands of compounds are screened in a high-throughput format for selective toxicity to engineered tumorigenic cells. In one embodiment of the invention, selective toxicity is determined by comparing cell viability of test cells, which are engineered tumorigenic cells, and control cells after contact with a candidate agent. An appropriate control is a cell that is the same type of cell as that of test cells except that the control cell is not engineered to be tumorigenic. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference). In certain embodiments, the candidate agent is selected from a compound library, such as a combinatorial library. Cell viability may be determined by any of a variety of means known in the art, including the use of dyes such as calcein acetoxymethyl ester (calcein AM) and Alamar Blue. In certain embodiments of the invention, a dye such as calcein AM is applied to test and control cells after treatment with a candidate agent. In live cells, calcein AM is cleaved by intracellular esterases, forming the anionic fluorescent derivative calcein, which cannot diffuse out of live cells. Hence, live cells exhibit a green fluorescence when incubated with calcein AM, whereas dead cells do not. The green fluorescence that is exhibited by live cells can be detected and can thereby provide a measurement of cell viability.

In certain embodiments of the invention, an agent that has been identified as one that selectively induces cell death in an engineered tumorigenic cell is further characterized in an animal model. Animal models include mice, rats, rabbits, and monkeys, which can be nontransgenic (e.g., wildtype) or transgenic animals. The effect of the agent that selectively induces cell death in engineered tumorigenic cells may be assessed in an animal model for any number of effects, such as its ability to selectively induce cell death in tumorigenic cells in the animal and its general toxicity to the animal. For example, the method can comprise further assessing the selective toxicity of an agent (drug) to tumorigenic cells in an appropriate mouse model.

The effect of the agent that induces death in engineered tumorigenic cells may be assessed in an animal model for any number of effects, such as its ability to induce death in tumorigenic cells in the animal and its general toxicity to the animal. For example, the method can comprise further assessing the toxicity of an agent (drug) to tumorigenic cells in an appropriate mouse model. To illustrate, an agent can be further evaluated by using a tumor growth regression assay which assesses the ability of tested agent to inhibit the growth of established solid tumors in mice. The assay can be performed by implanting tumor cells into the fat pads of nude mice. Tumor cells are then allowed to grow to a certain size before the agents are administered. The volumes of tumors are monitored for a set number of weeks, e.g., three weeks. General health of the tested animals is also monitored during the course of the assay.

In additional embodiments of the invention, an agent that has been identified as one that selectively kills or inhibits the growth/proliferation of engineered tumorigenic cells is further characterized in cell-based assays to assess its mechanism of action. For example, the agent may be tested in apoptosis assays to assess its ability to induce cell death by means of a pro-apoptotic pathway. In further embodiments of the invention, an agent that induces death in tumor cells is assessed for its ability to induce death in tumorigenic cells by a non-apoptotic pathway. For example, the agent may be tested in apoptosis assays to assess its inability to induce cell death by means of a pro-apoptotic pathway.

In other embodiments, the invention relates to a method of identifying agents (drugs) that selectively suppresses the cellular toxicity in engineered cells, for example, engineered neuronal cells expressing a mutant huntingtin protein. In one embodiment, the invention relates to a method of identifying an agent (drug) that suppresses the cellular toxicity of a mutant huntingtin protein in engineered cells, comprising contacting test cells (e.g., engineered neuronal cells expressing a mutant huntingtin protein) with a candidate agent; determining viability of the test cells contacted with the candidate agent; and comparing the viability of the test cells with the viability of an appropriate control. If the viability of the test cells is more than that of the control cells, then an agent (drug) that selectively suppresses the cellular toxicity (e.g., huntingtin-induced cellular toxicity) is identified. An appropriate control is a cell that is the same type of cell as that of test cells except that the control cell is not engineered to express a protein which causes toxicity. For example, control cells may be the parental primary cells from which the test cells are derived. Control cells are contacted with the candidate agent under the same conditions as the test cells. An appropriate control may be run simultaneously, or it may be pre-established (e.g., a pre-established standard or reference).

In certain embodiments, the genotype-selective compounds of the invention (anti-tumor agents or anti-HD agents) can be any chemical (element, molecule, compound, drug), made synthetically, made by recombinant techniques or isolated from a natural source. For example, these compounds can be peptides, polypeptides, peptoids, sugars, hormones, or nucleic acid molecules (such as antisense or RNAi nucleic acid molecules). In addition, these compounds can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. These compounds can also be natural or genetically engineered products isolated from lysates or growth media of cells—bacterial, animal or plant—or can be the cell lysates or growth media themselves. Presentation of these compounds to a test system can be in either an isolated form or as mixtures of compounds, especially in initial screening steps.

Genotype-Selective Compounds of the Invention

Applicants' results demonstrate that it is possible to identify compounds with increased potency and activity in the presence of specific genetic elements. Although previous reports indicated that it may be possible to identify such genotype-selective compounds in the case of one genetic element of interest (Simons et al., 2001, Genome Res 11, 266-73; Stockwell et al., 1999, Chem Biol 6, 71-83; Torrance et al., 2001, Nat Biotechnol 19, 940-5), work described herein provides a systematic testing of synthetic lethality using more than 23,000 compounds and one or more cancer-related genetic elements.

The nine selective compounds identified help to define consequences of introducing TERT and one or more of LT, ST, E6, E7 and oncogenic RAS into normal human cells. One effect of these genetic changes is to increase the rate of cell proliferation and to allow sensitivity to small molecules that inhibit DNA synthesis. Although it is well established that such agents preferentially target rapidly replicating tumor cells, it is reassuring to see this principle emerge from this unbiased screening approach. Moreover, the methodology made it possible to readily distinguish between compounds that have a clear basis for genetic selectivity and those that do not.

Results showed that expression of hTERT and either E7 or LT sensitizes cells to topoisomerase II poisons. Since loss or inactivation of RB (Sellers and Kaelin, 1997, J Clin Oncol 15, 3301-12; Sherr, 2001, Nat Rev Mol Cell Biol 2, 731-7) and activation of telomerase (Hahn and Weinberg, 2002, Nat Rev Cancer 2, 331-41; Harley, 1994, Pathol Biol (Paris) 42, 342-5) are found in most human cancers, these observations may explain, in part, the activity of these agents in a diverse range of human tumor types.

Applicants discovered that camptothecin is selectively lethal to cells harboring both ST and oncogenic RAS because of the combined effect of these two genes on expression of topoisomerase I. Rapidly dividing tumor cells use topoisomerase I to unwind supercoiled DNA to effect continuous and rapid cell division. When these two pathways are simultaneously altered, topoisomerase I is upregulated, perhaps indirectly, and such tumor cells are rendered sensitive to topoisomerase I poisons.

These observations suggest that one aspect of the ability of ST to transform human cells along with $RAS^{V12}$, LT and hTERT may be the effect of ST and $RAS^{V12}$ on expression of topoisomerase I. Mutations in HRAS and KRAS have been described in many types of human cancers. Moreover, the inactivation of PPP2R1B, a component of PP2A, has recently been reported in colon and lung tumors (Wang et al., 1998, Science 282, 284-7), while mutations in a different PP2A subunit have been described in melanoma, lung, breast and colon cancers (Calin et al., 2000, Oncogene 19, 1191-5; Kohno et al., 1999, Cancer Res 59, 4170-4; Ruediger et al., 2001, Oncogene 20, 1892-9; Ruediger et al., 2001, Oncogene 20, 10-5). At present, it remains unclear whether simultaneous alteration of these two pathways occurs at high frequency in human tumors or whether cancers in which both of these pathways are perturbed show increased susceptibility to these compounds.

Figure 8:
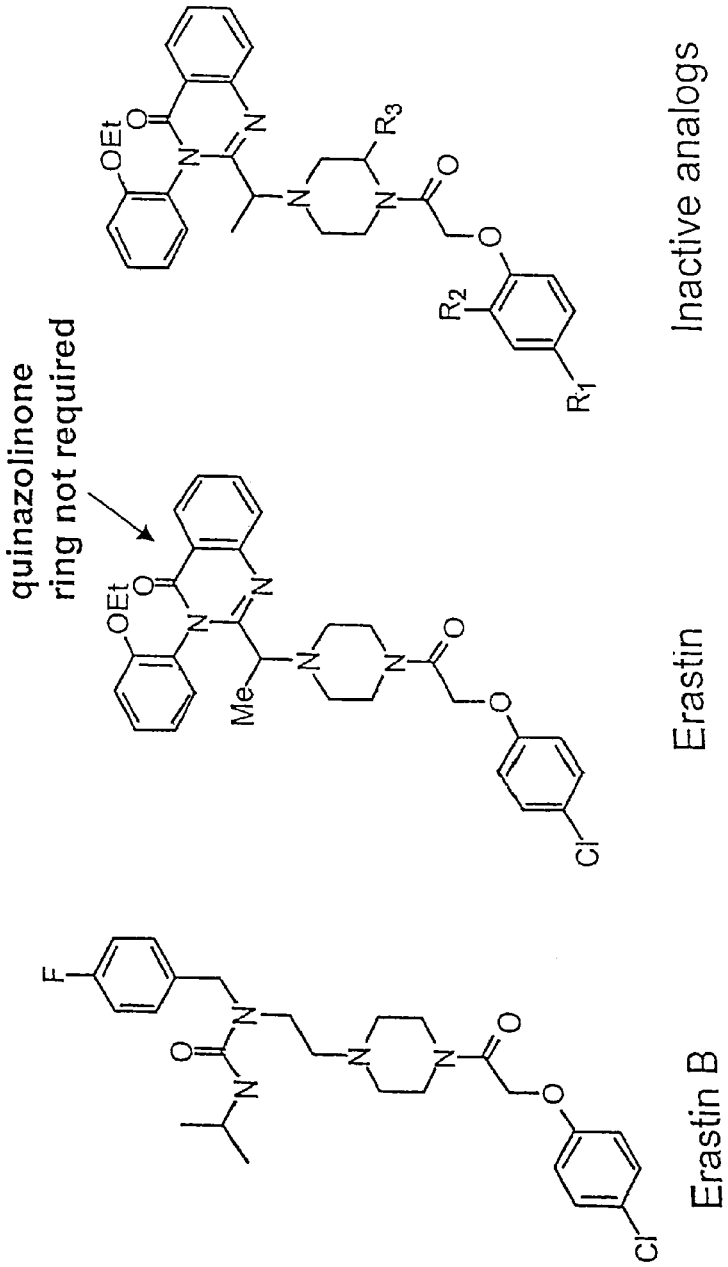
FIG. 8 shows the chemical structures of erastin and erastin B.

Further, Applicants identified a novel compound, which they named erastin (see FIG. 8), that is lethal to cells expressing both ST and $RAS^{V12}$. Treatment of cells with this compound failed to kill cells lacking $RAS^{V12}$ and ST, even when used at concentrations eight-fold higher than was required to observe an effect on cells expressing both $RAS^{V12}$ and ST, indicating a degree of specificity. The lethal effect of erastin is rapid and irreversible once obtained.

Erastin may be used to induce cell death in any tumor cell wherein contact of the tumor cell with erastin results in cell death. Tumorigenic cells in which lethality may be produced by erastin activity include not only engineered tumorigenic cells, such as engineered cells expressing both ST and $RAS^{V12}$, but also tumorigenic cells comprising an activated RAS pathway independent of ST and $RAS^{V12}$ expression.

Applicants additionally tested 135 analogs of erastin for activity and selectivity in tumor cells versus normal cells. 134 of these analogs were inactive. One was active and selective, but less potent than erastin. This compound was named erastin B (see FIG. 8). In certain embodiments of the invention, the invention relates to the compound, erastin. In further embodiments, the invention relates to analogs of the compound, erastin, which analogs exhibit selective toxicity to engineered tumorigenic cells, such as engineered human tumorigenic cells. In one embodiment, the analog of erastin, which exhibits selective toxicity to engineered human tumorigenic cells, is erastin B. In certain embodiments, the invention relates to a racemic mixture of a compound of the invention, which mixture exhibits selective toxicity to engineered tumorigenic cells.

For both camptothecin (CPT) and erastin, Applicants identified synergy between pathways altered by expression of $RAS^{V12}$ and ST. Expression of $RAS^{V12}$ leads to the activation of several well-characterized signaling pathways, including the RAF-MEK-MAPK signaling cascade, the phosphatidylinositol 3-kinase (PI3K) signaling pathway and the Ral-guanine dissociation factor pathway (Ral-GDS). Each of these pathways has been implicated in human cancers, and recent work demonstrates that these pathways work in concert in this system of cell transformation (Hamad et al., 2002, Genes Dev 16, 2045-57). In addition, ST binds to and inactivates PP2A, a widely expressed serine-threonine phosphatase. Although the specific enzymatic targets of PP2A that are perturbed upon expression of ST are not yet known, there is substantial overlap among pathways altered by PP2A and RAS (Millward et al., 1999, Trends Biochem Sci 24, 186-91). Understanding further the mechanism by which erastin induces death in cells harboring alterations of these two signaling pathways may provide clues to the nature and extent of functional overlap between these two pathways.

Figure 15:
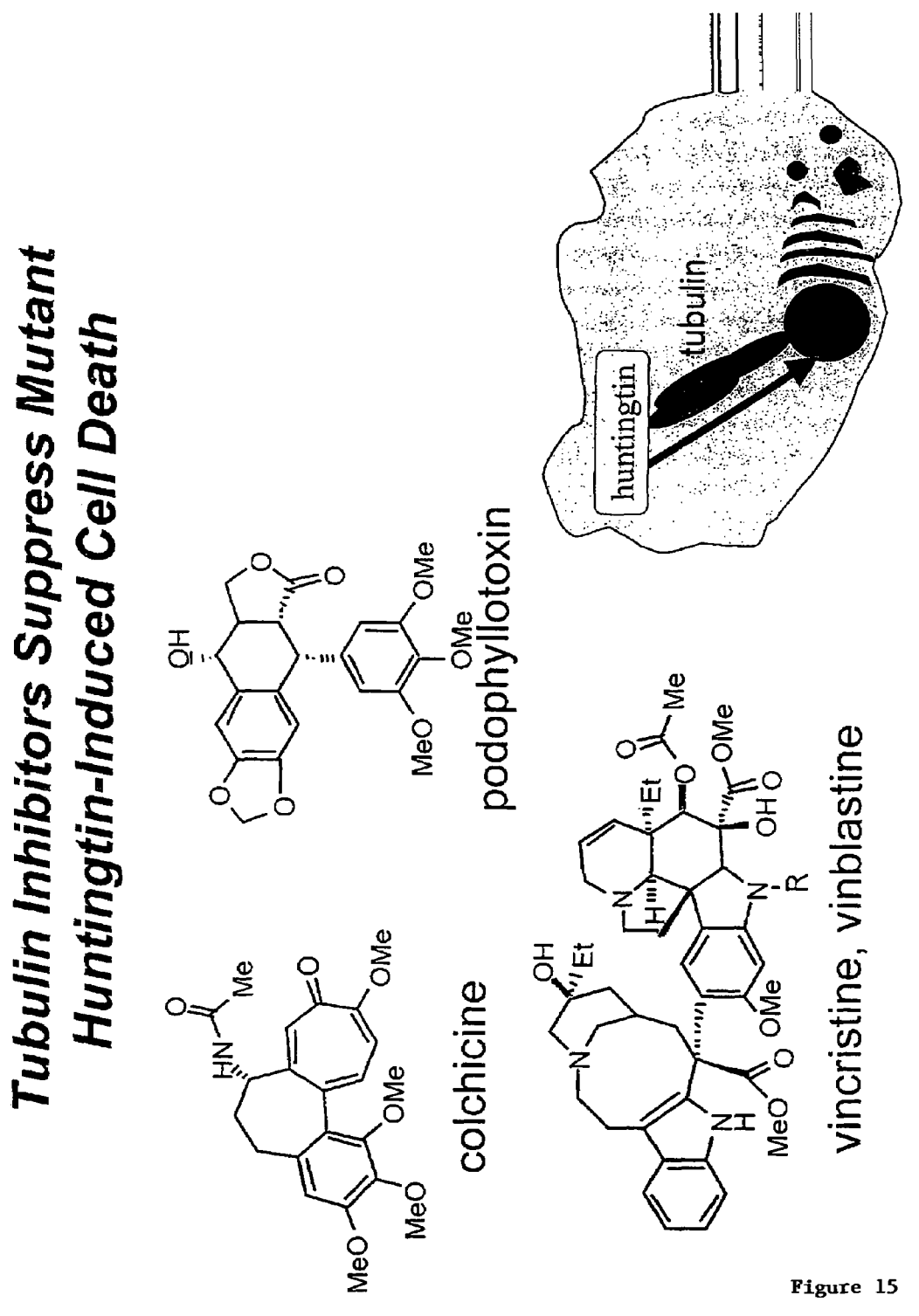

In other embodiments, Applicants have identified inhibitors (suppressors) of mutant huntingtin-induced neuronal cell death using the screening methods of the invention. By screening a library of ~2,500 biologically active compounds, 10 compounds were identified to selectively prevent mutant huntingtin-induced death of neuronal cells. In addition, a small number of compounds were identified to increase viability of mutant huntingtin-expressing neuronal cells as well as wild-type huntingtin-expressing cells and/or parental cells. These suppressors of mutant huntingtin-induced neuronal cell death include, but are not limited to, tubulin inhibitors (e.g., those shown in FIG. 15).

Methods of Identifying Targets for Genotype-Selective Compounds

In certain embodiments, the invention relates to the use of the subject genotype-selective compound, also referred to herein as "ligand" (e.g., erastin), to identify targets (also referred to herein as "cellular components" (e.g., proteins, nucleic acids, or lipids) involved in conferring the phenotype of diseased cells.

In one embodiment, the invention provides a method to identify cellular components involved in tumorigenesis, whereby a tumorigenic cell, such as an engineered human tumorigenic cell, is contacted with a subject anti-tumor compound; and after contact, cellular components that interact (directly or indirectly) with erastin are identified, resulting in identification of cellular components involved in tumorigenesis. In another embodiment, the invention provides a method to identify cellular components involved in tumorigenesis. In this method, (a) a tumorigenic cell, such as an engineered human tumorigenic cell, is contacted with an inhibitor of erastin and contacted with erastin; and (b) cellular components that interact (directly or indirectly) with the inhibitor of erastin are identified, which cellular components are involved in tumorigenesis. The cell can be contacted with erastin and the inhibitor of erastin sequentially or simultaneously. Cellular components that interact with erastin or any agent of the present invention may be identified by known methods.

In a further embodiment, the invention provides a method to identify cellular components involved in HD, whereby a cell having huntingtin-induced toxicity, such as an engineered neuronal cell, is contacted with an anti-HD test compound; and after contact, cellular components that interact (directly or indirectly) with the anti-HD test compound are identified, resulting in identification of cellular components involved in HD.

As described herein, the subject compound (or ligand) of these methods may be created by any combinatorial chemical method. Alternatively, the subject compound may be a naturally occurring biomolecule synthesized in vivo or in vitro. The ligand may be optionally derivatized with another compound. One advantage of this modification is that the derivatizing compound may be used to facilitate ligand target complex collection or ligand collection, e.g., after separation of ligand and target. Non-limiting examples of derivatizing groups include biotin, fluorescein, digoxygenin, green fluorescent protein, isotopes, polyhistidine, magnetic beads, glutathione S transferase, photoactivatible crosslinkers or any combinations thereof.

According to the present invention, a target (cellular component) may be a naturally occurring biomolecule synthesized in vivo or in vitro. A target may be comprised of amino acids, nucleic acids, sugars, lipids, natural products or any combinations thereof. An advantage of the instant invention is that no prior knowledge of the identity or function of the target is necessary.

The interaction between the ligand and target may be covalent or non-covalent. Optionally, the ligand of a ligand-target pair may or may not display affinity for other targets. The target of a ligand-target pair may or may not display affinity for other ligands.

For example, binding between a ligand and a target can be identified at the protein level using in vitro biochemical methods, including photo-crosslinking, radiolabeled ligand binding, and affinity chromatography (Jakoby W B et al., 1974, Methods in Enzymology 46: 1). Alternatively, small molecules can be immobilized on an agarose matrix and used to screen extracts of a variety of cell types and organisms.

Expression cloning can be used to test for the target within a small pool of proteins (King R W et. al., 1997, Science 277:973). Peptides (Kieffer et. al., 1992, PNAS 89:12048), nucleoside derivatives (Haushalter K A et. al., 1999, Curr. Biol. 9:174), and drug-bovine serum albumin (drug-BSA) conjugate (Tanaka et. al., 1999, Mol. Pharmacol. 55:356) have been used in expression cloning.

Another useful technique to closely associate ligand binding with DNA encoding the target is phage display. In phage display, which has been predominantly used in the monoclonal antibody field, peptide or protein libraries are created on the viral surface and screened for activity (Smith G P, 1985, Science 228:1315). Phages are panned for the target which is connected to a solid phase (Parmley S F et al., 1988, Gene 73:305). One of the advantages of phage display is that the cDNA is in the phage and thus no separate cloning step is required.

A non-limiting example includes binding reaction conditions where the ligand comprises a marker such as biotin, fluorescein, digoxygenin, green fluorescent protein, radioisotope, histidine tag, a magnetic bead, an enzyme or combinations thereof. In one embodiment of the invention, the targets may be screened in a mechanism based assay, such as an assay to detect ligands which bind to the target. This may include a solid phase or fluid phase binding event with either the ligand, the protein or an indicator of either being detected. Alternatively, the gene encoding the protein with previously undefined function can be transfected with a reporter system (e.g., β-galactosidase, luciferase, or green fluorescent protein) into a cell and screened against the library preferably by a high throughput screening or with individual members of the library. Other mechanism based binding assays may be used, for example, biochemical assays measuring an effect on enzymatic activity, cell based assays in which the target and a reporter system (e.g., luciferase or β-galactosidase) have been introduced into a cell, and binding assays which detect changes in free energy. Binding assays can be performed with the target fixed to a well, bead or chip or captured by an immobilized antibody or resolved by capillary electrophoresis. The bound ligands may be detected usually using colorimetric or fluorescence or surface plasmon resonance.

In certain embodiments, the present invention further contemplates methods of treating or preventing a disease (e.g., cancer or HD) by modulating the function (e.g., activity or expression) of a target (cellular component) that is identified according to the invention. To illustrate, if a target is identified to promote tumor growth, a therapeutic agent can be used to inhibit or reduce the function (activity or expression) of the target. Alternatively, if a target is identified to inhibit tumor growth, a therapeutic agent can be used to enhance the function (activity or expression) of the target. The therapeutic agent includes, but is not limited to, an antibody, a nucleic acid (e.g., an antisense oligonucleotide or a small inhibitory RNA for RNA interference), a protein, a small molecule or a peptidomimetic.

Methods of Treatment

In certain embodiments, the invention provides a method to treat or prevent cancer in an individual. The terms "cancer," "tumor," and "neoplasia" are used interchangeably herein. As used herein, a cancer (tumor or neoplasia) is characterized by one or more of the following properties: cell growth is not regulated by the normal biochemical and physical influences in the environment; anaplasia (e.g., lack of normal coordinated cell differentiation); and in some instances, metastasis. Cancer diseases include, for example, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. Additional cancer disorders can be found in, for example, Isselbacher et al. (1994) Harrison's Principles of Internal Medicine 1814-1877, herein incorporated by reference.

In one embodiment, the invention relates to a method of treating or preventing cancer in an individual, comprising administering to the individual a therapeutically effective amount of a compound that is selectively toxic to an engineered human tumorigenic cell. In certain embodiments, the cancer is characterized by cells comprising an activated RAS pathway. In certain further embodiments, the cancer is characterized by cells expressing SV40 small T oncoprotein and/or oncogenic HRAS.

In a related embodiment, the invention contemplates the practice of the method in conjunction with other anti-tumor therapies such as conventional chemotherapy directed against solid tumors and for control of establishment of metastases. The administration of the compounds of the invention can be conducted during or after chemotherapy.

A wide array of conventional compounds have been shown to have anti-tumor activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-tumor compounds induce undesirable side effects. In many cases, when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Therefore, pharmaceutical compositions of the present invention may be conjointly administered with a conventional anti-tumor compound. Conventional anti-tumor compounds include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In another related embodiment, the invention contemplates the practice of the method in conjunction with other anti-tumor therapies such as radiation. As used herein, the term "radiation" is intended to include any treatment of a neoplastic cell or subject by photons, neutrons, electrons, or other type of ionizing radiation. Such radiations include, but are not limited to, X-ray, gamma-radiation, or heavy ion particles, such as alpha or beta particles. Additionally, the radiation may be radioactive. The means for irradiating neoplastic cells in a subject are well known in the art and include, for example, external beam therapy, and brachytherapy.

Methods to determine if a cancer (tumor or neoplasia) has been treated are well known to those skilled in the art and include, for example, a decrease in the number of tumor cells (e.g., a decrease in cell proliferation or a decrease in tumor size). It is recognized that the treatment of the present invention may be a lasting and complete response or can encompass a partial or transient clinical response. See for example, Isselbacher et al. (1996) Harrison's Principles of Internal Medicine 13 ed., 18141882, herein incorporated by reference.

Assays to test for the sensitization or the enhanced death of tumor cells are well known in the art, including, for example, standard dose response assays that assess cell viability; agarose gel electrophoresis of DNA extractions or flow cytometry to determine DNA fragmentation, a characteristic of cell death; assays that measure the activity of polypeptides involved in apoptosis; and assay for morphological signs of cell death. The details regarding such assays are described elsewhere herein. Other assays include, chromatin assays (e.g., counting the frequency of condensed nuclear chromatin) or drug resistance assays as described in, for example, Lowe et al. (1993) Cell 74:95 7-697, herein incorporated by reference. See also U.S. Pat. No. 5,821,072, also herein incorporated by reference.

In other embodiments, the invention provides a method to treat or prevent a neurodegenerative disorder associated with polyglutamine (polyQ) expansion, in an individual. This method comprises administering to the individual a therapeutically effective amount of an agent identified by the methods of the invention as described above. As described herein, the neurodegenerative disorders associated with polyQ expansion include, but are not limited to, Huntington's disease, spinobulbar muscular atrophy, dentatorubral pallidoluysian atrophy, and the spinocerebellar ataxias type 1, 2, 3, 6, 7, and 17. For example, a tubulin inhibitor can be administrated to an individual suffering from HD or at risk of HD, for therapeutic or prophylactic purposes.

Pharmaceutical Compositions

A compound of the present invention, such as erastin or a tubulin inhibitor, may be administered to an individual in need thereof. In certain embodiments, the individual is a mammal such as a human. When administered to an individual, the compound of the invention can be administered as a pharmaceutical composition (preparation) containing, for example, the compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable agents that act, for example, to stabilize or to increase the absorption of a compound such as erastin or a tubulin inhibitor. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition (preparation) also can be a liposome or other polymer matrix, which can have incorporated therein, for example, a compound of the invention. Liposomes, for example, which consist of phospholipids or other lipids, are nontoxic, physiologically acceptable and metabolizable carriers that are relatively simple to make and administer.

A pharmaceutical composition (preparation) containing a compound of the invention can be administered to a subject by any of a number of routes of administration including, for example, orally; intramuscularly; intravenously; anally; vaginally; parenterally; nasally; intraperitoneally; subcutaneously; and topically. The composition can be administered by injection or by incubation.

In certain embodiments, the compound (e.g., erastin) of the present invention may be used alone or conjointly administered with another type of anti-tumor therapeutic agent. As used herein, the phrase "conjoint administration" refers to any form of administration in combination of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. Thus, an individual who receives such treatment can have a combined (conjoint) effect of different therapeutic compounds.

It is contemplated that the compound (e.g., erastin) of the present invention will be administered to a subject (e.g., a mammal, preferably a human) in a therapeutically effective amount (dose). By "therapeutically effective amount" is meant the concentration of a compound that is sufficient to elicit the desired therapeutic effect (e.g., the death of a neoplastic cell). It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. Typically, for a human subject, an effective amount will range from about 0.001 mg/kg of body weight to about 30 mg/kg of body weight. A larger total dose can be delivered by multiple administrations of the agent. Methods to determine efficacy and dosage are known to those skilled in the art. See, for example, Isselbacher et al. (1996) Harrison's Principles of Internal Medicine 13 ed., 1814-1882, herein incorporated by reference.

EXEMPLIFICATION

The invention now being generally described, it will be more readily understood by reference to the following examples, which are included merely for purposes of illustration of certain aspects and embodiments of the present invention, and are not intended to limit the invention.

Example 1 Identification of Compounds with Increased Potency or Activity in the Presence of Specific Cancer-Related Alleles Work described herein has provided a link between ST and $RAS^{V12}$ signaling and a rapid and selective, non-apoptotic cell death pathway operative in human fibroblasts. Identifying novel mechanisms for killing tumor cells, particularly in a genotype-selective fashion, would be of value for understanding tumor cell biology and development of new classes of anti-tumor agents. Some have argued that most existing anti-tumor agents kill tumor cells via apoptosis (Makin, 2002, Expert Opin Ther Targets 6, 73-84), highlighting the potential importance of the finding that erastin acts through a novel, non-apoptotic pathway. The discovery of these signaling interactions was made possible by the combined use of chemical genetic and molecular genetic approaches to tumor cell biology. Although work described herein made use of hTERT, LT, ST, E6, E7 and $RAS^{V12}$ as transforming genes, future studies can make use of a wide variety of cancer-associated alleles using this methodology in order to define the signaling networks that involve many oncogenes and tumor suppressors. Such studies may ultimately unravel details of these and other critical signaling networks altered by oncogenic mutations.

Described here is work carried out to identify compounds with increased potency or activity in the presence of hTERT, LT, ST, E6, E7 or $RAS^{V12}$. Engineered cell lines with these genetic elements were used to screen 23,550 compounds, including 20,000 compounds from a combinatorial library, 1,990 compounds from the National Cancer Institute diversity collection, and 1,540 biologically active known compounds that were selected and purchased by Applicant and formatted into a screenable collection. The primary screen tested (in quadruplicate) the effect of treating tumorigenic BJ-TERT/LT/ST/$RAS^{V12}$ engineered tumorigenic cells with each compound for 48 hours at a concentration of 4 µg/mL, corresponding to 10 µM for a compound with a molecular weight of 400, which is the approximate median molecular weight of the libraries. Cell viability was measured using the dye calcein acetoxymethyl ester (calcein AM) (Wang et al., 1993, Hum. Immunol. 37, 264-270), which is a non-fluorescent compound that freely diffuses into cells. In live cells, calcein AM is cleaved by intracellular esterases, forming the anionic fluorescent derivative calcein, which cannot diffuse out of live cells. Hence, live cells exhibit a green fluorescence when incubated with calcein AM, whereas dead cells do not. Compounds that displayed 50% or greater inhibition of staining with the viability dye calcein AM in BJ-TERT/LT/ST/$RAS^{V12}$ cells were subsequently tested in a two-fold dilution series in BJ and BJ-TERT/LT/ST/$RAS^{V12}$ cells to identify compounds that display synthetic lethality, which is lethality in tumorigenic cells but not in isogenic primary cells. The $IC_{50}$ value (concentration required to inhibit 50% of the calcein AM signal) was calculated for each compound in each cell line (Table 1). This resulted in identification of nine compounds (FIG. 2) that were at least four-fold more potent in BJ-TERT/LT/ST/$RAS^{V12}$ tumorigenic cells relative to BJ primary cells (compounds for which at least a four-fold higher concentration was required in BJ primary cells in order to obtain the same 50% inhibition of calcein AM signal). Following is a more detailed analysis of these nine compounds.

Three of these compounds (doxorubicin, daunorubicin and mitoxantrone) are in current clinical use as anti-cancer drugs, one (camptothecin) is a natural product analog of clinically used anticancer drugs (topotecan and irinotecan), and one (echinomycin) was recently tested in phase II clinical trials. All nine compounds were subsequently tested in replicate at multiple doses in each panel of engineered cells to confirm that the observed selectivities were seen in multiple independently-derived cell lines (FIG. 1 and Table 1).

Applicants developed a selectivity metric that measures the shift in the $IC_{50}$ (concentration required for 50% inhibition of viability signal) of a compound in two different cell lines. To calculate this selectivity score between two cell lines, the $IC_{50}$ for a compound in one cell line was divided by the $IC_{50}$ for the same compound in a second cell line. Thus, a compound that must be used at a four-fold higher concentration in one cell line relative to a second cell line would have a selectivity score of 4. The "tumor selectivity score" was calculated for each compound, by dividing the $IC_{50}$ value for the compound in the parental, primary BJ cells by the $IC_{50}$ value for the compound in engineered BJ-TERT/LT/ST/RAS$^{V12}$ cells, containing all four genetic elements required to create tumorigenic cells (Table 1).

These engineered tumorigenic cells make use of dominantly acting viral oncoproteins such as LT, ST, E6 and E7. These viral proteins are possibly involved in cell transformation in specific forms of cancer, namely simian virus 40-induced malignant mesothelioma (Testa and Giordano, 2001, Semin Cancer Biol 11, 31-8) and human papillomavirus-induced cervical carcinoma (Bosch et al., 2002, J Clin Pathol 55, 244-65), and have been used to disrupt p53 and pRB function to transform cells in vitro and in vivo (Elenbaas et al., 2001, Genes Dev 15, 50-65; Jorcyk et al., 1998, Prostate 34, 10-22; Perez-Stable et al., 1997, Cancer Res 57, 900-6; Rich et al., 2001, Cancer Res 61, 3556-60; Sandmoller et al., 1995, Cell Growth Differ 6, 97-103). Applicants made use of these two different methods for inactivating cellular proteins, (they tested the effects of both LT and E6/E7-based inactivation of pRB and p53) in order to control for idiosyncratic effects that might be observed with a specific viral protein. The selectivity of these compounds was also confirmed in a cell line expressing dominant negative inhibitors of p53 and pRB that are not derived from viral elements. This cell line expresses (i) a truncated form of p53 (p53DD) that disrupts tetramerization of endogenous p53, (ii) a CDK4$^{R24C}$ mutant resistant to inhibition by p16$^{INK4A}$ and p15$^{INK4B}$ (the major negative regulators of CDK4) and (iii) cyclin D1. The effects of the nine genotype-selective compounds were tested at a range of concentrations in these cells, which are referred to as BJ-TERT/p53DD/CDK4$^{R24C}$/D1/ST/RAS$^{V12}$ cells (Table 1). Results showed that there was an overall modest reduction in activity for all of the compounds when tested in these cells. However, the overall results of the analysis were unchanged by the use of non-viral proteins in this cell line (Table 1).

Example 2 Determination of the Genetic Basis of the Selectivity of Compounds

Applicants sought to determine the genetic basis of selectivity for each compound. That is, for each compound, they attempted to define the gene or combination of genes responsible for rendering cells sensitive to the compound (Table 1). Results showed that these nine compounds could be categorized into three groups, namely (i) compounds that displayed no simple genetic selectivity, (ii) compounds that displayed selectivity for cells harboring TERT and inactive RB, and (iii) compounds that required the presence of both oncogenic RAS and ST in order to exhibit lethality.

Figure 2:
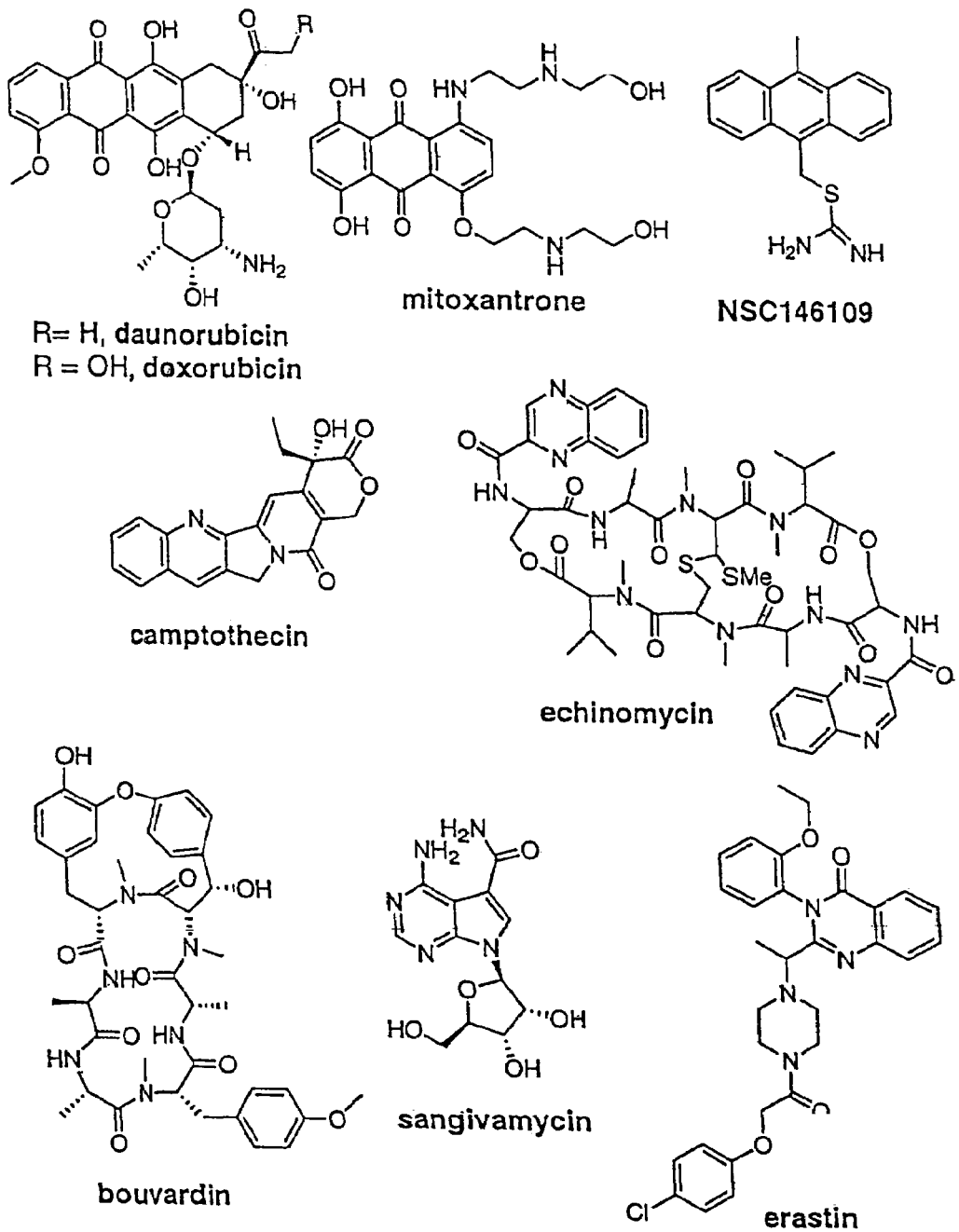
FIG. 2 shows the chemical structures of nine genotype-selective compounds.

The compounds in group (i), sangivamycin, bouvardin, NSC146109 and echinomycin, have no clear genetic basis for their tumorigenic cell selectivity. For example, echinomycin becomes somewhat more active as each genetic element is introduced (FIG. 3a). Applicants have observed that the rate of cell proliferation increases when each of these genetic elements is introduced. Thus, it is likely that the compounds in group (i) are simply selective for rapidly dividing cells. Supporting this interpretation is the fact that all of these compounds are reported to act by inhibiting DNA or protein synthesis, the need for which is greater in rapidly dividing cells. For example, echinomycin is reported to function as a DNA bis-intercalator (Van Dyke and Dervan, 1984, Science 225, 1122-7; Waring and Wakelin, 1974, Nature 252, 653-7), bouvardin is reported to function as a protein synthesis inhibitor (Zalacain et al., 1982, FEBS Lett 148, 95-7), sangivamycin is a nucleotide analog (Rao, 1968, J Med Chem 11, 939-41), and NSC146109 structurally resembles a DNA intercalator (FIG. 2). It should be noted that sangivamycin has been reported to function as a PKC inhibitor (Loomis and Bell, 1988, J Biol Chem 263, 1682-92), although this activity seems unlikely to be relevant in this context because other PKC inhibitors displayed no selectivity in this system. Applicants were able to identify compounds that are simply more active in rapidly dividing cells, such as these group (i) compounds, because they show no clear genetic basis of selectivity. No further work was done with these compounds. Thus, they were able to focus the mechanistic studies on the compounds in groups (ii) and (iii), which displayed selectivity.

The compounds in group (ii), mitoxantrone, doxorubicin and daunorubicin, are topoisomerase II poisons, which bind to topoisomerase II and DNA and prevent the religation of double strand DNA breaks introduced by topoisomerase II. These compounds, and anthracyclines in general, have also been reported to induce the formation of reactive oxygen species (ROS) in some cell types (Laurent and Jaffrezou, 2001, Blood 98, 913-24; Muller et al., 1998, Int J Mol Med 1, 4914; Richard et al., 2002, Leuk Res 26, 927-31), although Applicants did not observe the formation of ROS in these engineered cells in the presence of these three compounds. They discovered that these compounds become more potent (active at a lower concentration) when hTERT is introduced and again when RB is inactivated by introduction of LT or HPV E7. In the cells, E7 was introduced after E6, so it is possible that the increased potency of these compounds in cells harboring E7 also relies on the presence of E6, even though E6 by itself does not confer increased potency to these compounds. Introduction of hTERT and inactivation of RB caused an increase in topoisomerase IIα expression (FIG. 5A) and only a very modest increase in topoisomerase IIβ expression. Introduction of oncogenic RAS causes a further increase in topoisomerase IIα expression, although Applicants did not observe a further sensitization to the topoisomerase II poisons in the presence of oncogenic RAS (FIG. 5A).

Figure 3:
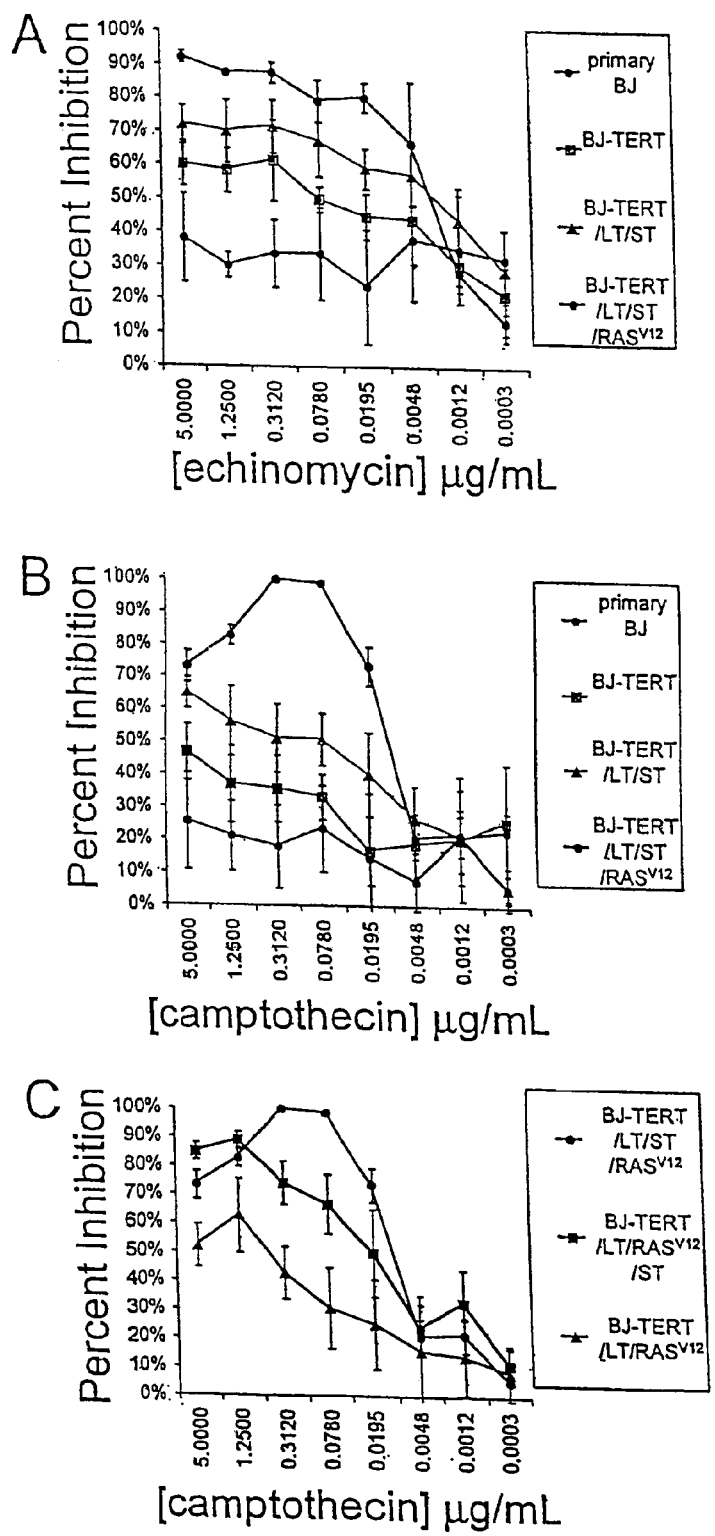
FIGS. 3A-3C are graphic representations of the effect of echinomycin and camptothecin on engineered cells. The indicated cells were treated with echinomycin (A) or camptothecin (B, C) in 384-well plates for 48 hours. Percent inhibition of cell viability, measured using calcein AM, is shown. Error bars indicate one standard deviation. (A) Echinomycin-treated BJ, BJ-TERT, BJ-TERT/LT/ST and BJ-TERT/LT/ST/RAS$^{V12}$ cells; (B) camptothecin-treated BJ, BJ-TERT, BJ-TERT/LT/ST and BJ-TERT/LT/ST/RAS$^{V12}$ cells; and (C) camptothecin-treated BJ-TERT/LT/RAS$^{V12}$, BJ-TERT/LT/RAS$^{V12}$/ST and BJ-TERT/LT/ST/RAS$^{V12}$ cells.
Figure 4:
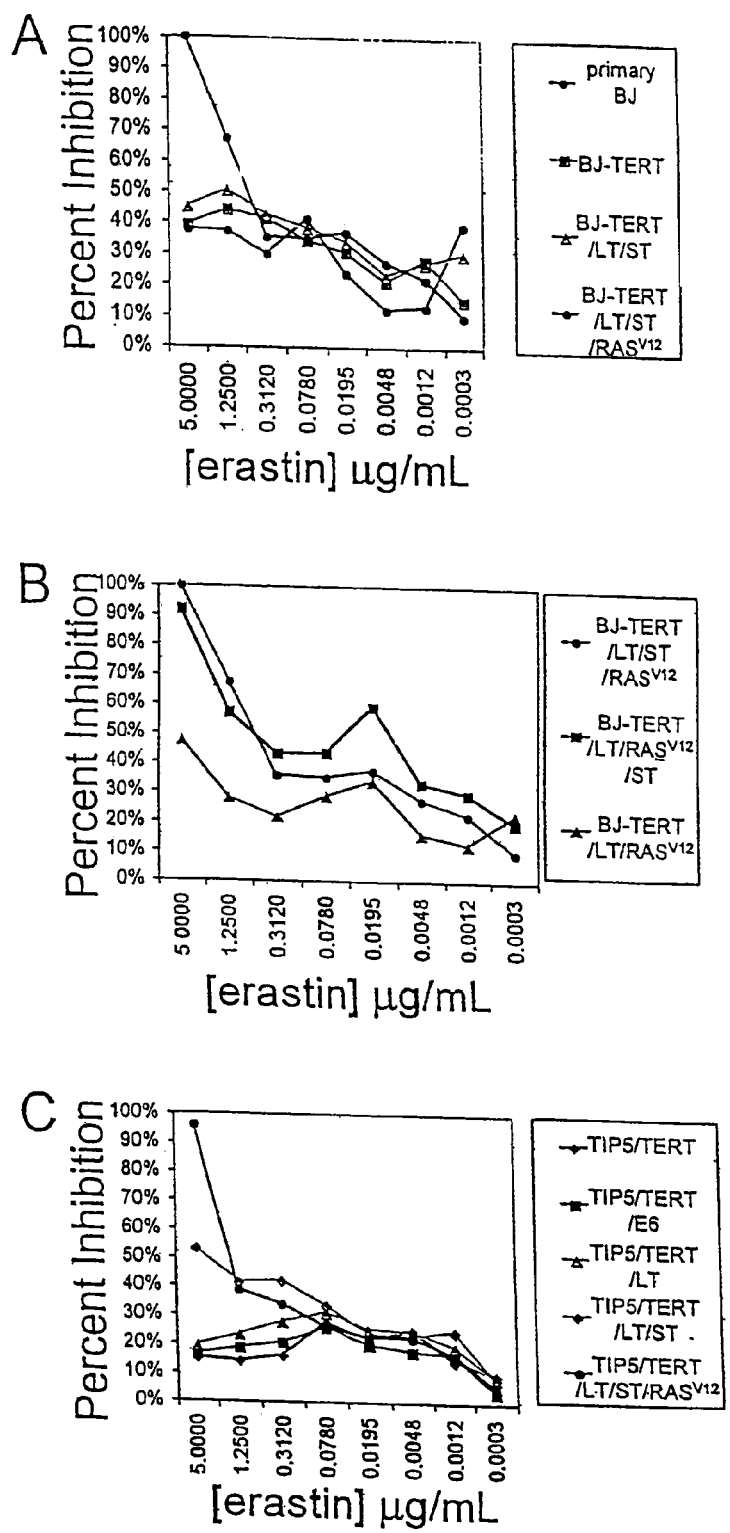
FIGS. 4A-4C are graphic representations of the effect of erastin on engineered cells. The indicated cells were treated with erastin in 384-well plates for 48 hours. Percent inhibition of cell viability, measured using calcein AM, is shown. Error bars indicate one standard deviation. (A) Erastin-treated BJ, BJ-TERT, BJ-TERT/LT/ST and BJ-TERT/LT/ST/RAS$^{V12}$ cells; (B) erastin-treated BJ-TERT/LT/RAS$^{V12}$ cells (lacking ST), BJ-TERT/LT/RAS$^{V12}$/ST (tumorigenic cells) and BJ-TERT/LT/ST/RAS$^{V12}$ (tumorigenic cells); and (C) independently derived TIP5/TERT, TIP5/TERT/E6, TIP5/TERT/LT, TIP5/TERT/LT/ST and TIP5/TERT/LT/ST/RAS$^{V12}$ cells.

The compounds in group (iii) are camptothecin (CPT) and a novel compound from a combinatorial library, which Applicants have named erastin, for eradicator of RAS and ST-expressing cells (FIG. 2). Efficient CPT-induced and erastin-induced cell death requires the presence of both ST and RAS$^{V12}$ (FIGS. 3 and 4 and Table 1). Although CPT and erastin have a similar genetic basis of selectivity, they have distinct mechanisms of action. CPT is partially active in cells lacking RB function (via expression of E7), whereas erastin is not, and CPT requires two days to cause death in BJ-TERT/LT/ST/RAS$^{V12}$ cells, while erastin is 100% effective within 18 hours (FIGS. 3 and 4). The phosphatase inhibitor okadaic acid was capable of sensitizing otherwise resistant BJ primary cells to CPT (FIG. 5E), possibly because okadaic acid upregulates TOP1 (FIG. 5F). Okadaic acid does not render BJ or BJ-TERT cells sensitive to erastin, consistent with a model in which CPT and erastin act via distinct mechanisms. Moreover, Applicants found that the lethal compound podophyllotoxin, a tubulin inhibitor, does not sensitize BJ or BJ-TERT cells to CPT, confirming that the sensitization of BJ cells to CPT by okadaic acid is specific and not the result of two weak cell death stimuli having an additive, but functionally irrelevant, effect.

Figure 5:
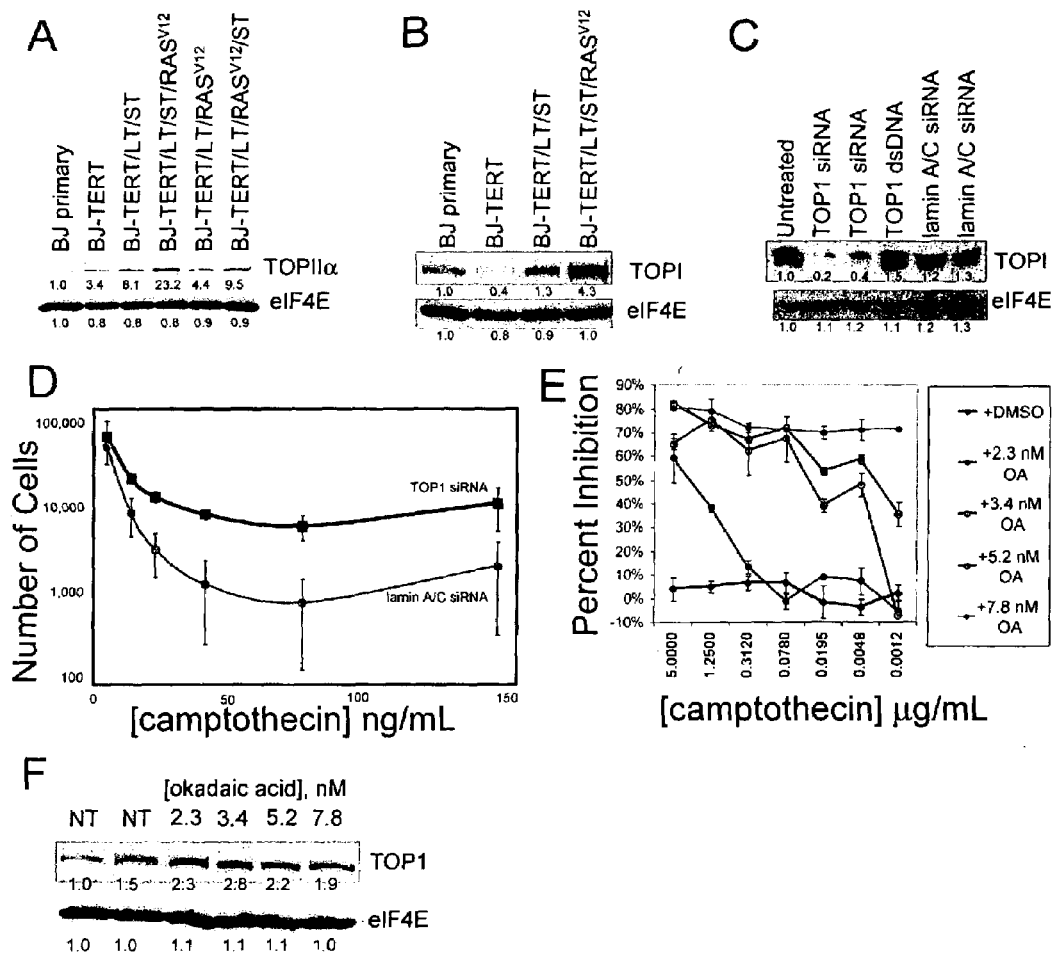
FIGS. 5A-5F show that protein targets of tumor-selective compounds are upregulated in engineered tumorigenic cells. (A-C) Western blot of lysates from BJ, BJ-TERT, BJ-TERT/LT/ST, BJ-TERT/LT/ST/RAS$^{V12}$, BJ-TERT/LT/RAS$^{V12}$ and BJ-TERT/LT/RAS$^{V12}$/ST cells with an antibody directed against topoisomerase II (A) or TOPI (B, C). In panel (C), cells were transfected with an siRNA directed against TOPI, lamic A/C or with a control double strand DNA duplex of the same length (TOPI dsDNA). In each case, the blot was probed with an antibody against eIF-4E to identify differences in the amount of protein loaded. The relative amount is quantitated below each band. (D) A TOPI siRNA prevents cell death caused by camptothecin in engineered tumor cells. Cell number was determined after transfection with an siRNA directed against TOPI and treatment with the indicated concentrations of camptothecin. (E) Okadaic acid, an inhibitor of PP2A and other cellular phosphatases, sensitizes primary human cells to camptothecin. BJ primary cells were treated simultaneously with the indicated concentrations of both camptothecin and okadaic acid and the effect on calcein AM viability staining was determined. Although okadaic acid kills BJ cells at the highest concentrations tested, at 3.4 nM it has no effect on its own, but it renders BJ cells sensitive to camptothecin. (F) Okadaic acid stimulates expression of TOP1. BJ primary cells were treated with the indicated concentrations of okadaic acid and the expression level of TOPI was determined by western blot. The relative amount is quantitated below each band.

In attempting to understand the molecular basis for the increased sensitivity to CPT of $RAS^{V12}$ and ST-expressing cells, Applicants determined the expression level in the engineered cells of topoisomerase I (TOP1), the putative target of CPT (Andoh et al., 1987, Proc Natl Acad Sci USA 84, 5565-9; Bjornsti et al., 1989, Cancer Res 49, 6318-23; Champoux, 2000, Ann N Y Acad Sci 922, 56-64; D'Arpa et al., 1990, Cancer Res 50, 6919-24; Eng et al., 1988, Mol Pharmacol 34, 755-60; Hsiang et al., 1989, Cancer Res 49, 5077-82; Hsiang and Liu, 1988, Cancer Res 48, 1722-6; Liu et al., 2000, Ann N Y Acad Sci 922, 1-10; Madden and Champoux, 1992, Cancer Res 52, 525-32; Tsao et al., 1993, Cancer Res 53, 5908-14). They discovered that cells expressing both $RAS^{V12}$ and ST upregulate TOP1 (FIG. 5B). As CPT's putative mechanism of action in other cell types involves a gain of function, namely introduction of double strand DNA breaks in a TOP1-dependent manner (Liu et al., 2000, Ann N Y Acad Sci 922, 1-10), upregulation of TOP1 could explain the increased sensitivity of $RAS^{V12}$ and ST-expressing cells to CPT. In support of this interpretation, they found that genetic inactivation of TOP1 with a small interfering RNA (siRNA) in BJ-TERT/LT/ST/$RAS^{V12}$ cells confers partial resistance to CPT (FIG. 5 C, D).

Applicants additionally tested 135 analogs of erastin for activity and selectivity in tumor cells versus normal cells. 134 of these analogs were inactive. One was active and selective, but less potent than erastin. This compound was named erastin B (see FIG. 8). See Tables II and III for examples of analogs of erastin that did not display activity or selectivity in tumor cells (BJELR cells) versus normal cells (BJEH cells). BJELR cells are BJ-TERT/LT/ST/$RAS^{V12}$ cells, and BJEH are BJ-TERT cells. The compounds listed in Table IV were also tested but did not show activity or selectivity in tumor cells versus normal cells.

Example 3 Characterization of Cell Death

Figure 7:
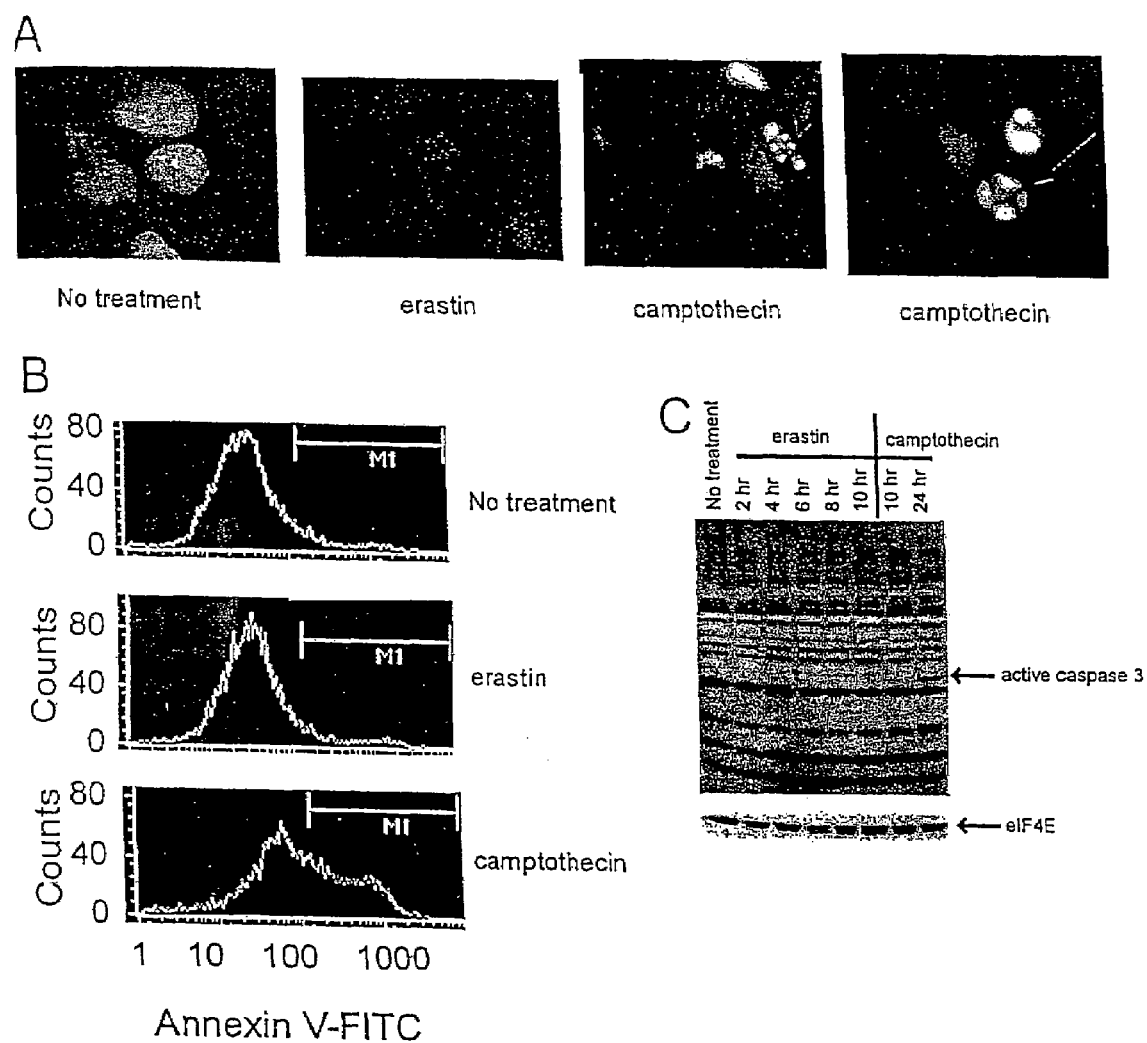
FIGS. 7A-7C show that camptothecin, but not erastin, induces characteristics of apoptosis. (A) Camptothecin-treated, but not erastin-treated, BJ-TERT/LT/ST/RAS$^{V12}$ cells displayed fragmented nuclei (10-20% of total nuclei, red and blue arrows) as shown. (B) Camptothecin-treated, but not erastin-treated, BJ-TERT/LT/ST/RAS$^{V12}$ cells display Annexin V staining. The percentage of cells in the indicated M1 region were 6%, 6% and 38% in untreated, erastin-treated (9 μM) and camptothecin-treated (1 μM), respectively. (C) Camptothecin-treated, but not erastin-treated, BJ-TERT/LT/ST/RAS$^{V12}$ cells harbor activated caspase 3. Lysates of camptothecin and erastin treated samples were analyzed by western blot with an antibody directed against the active, cleaved form of caspase 3. The blot was reprobed with an antibody directed against eIF4E to control for loading levels.
Figure 9:
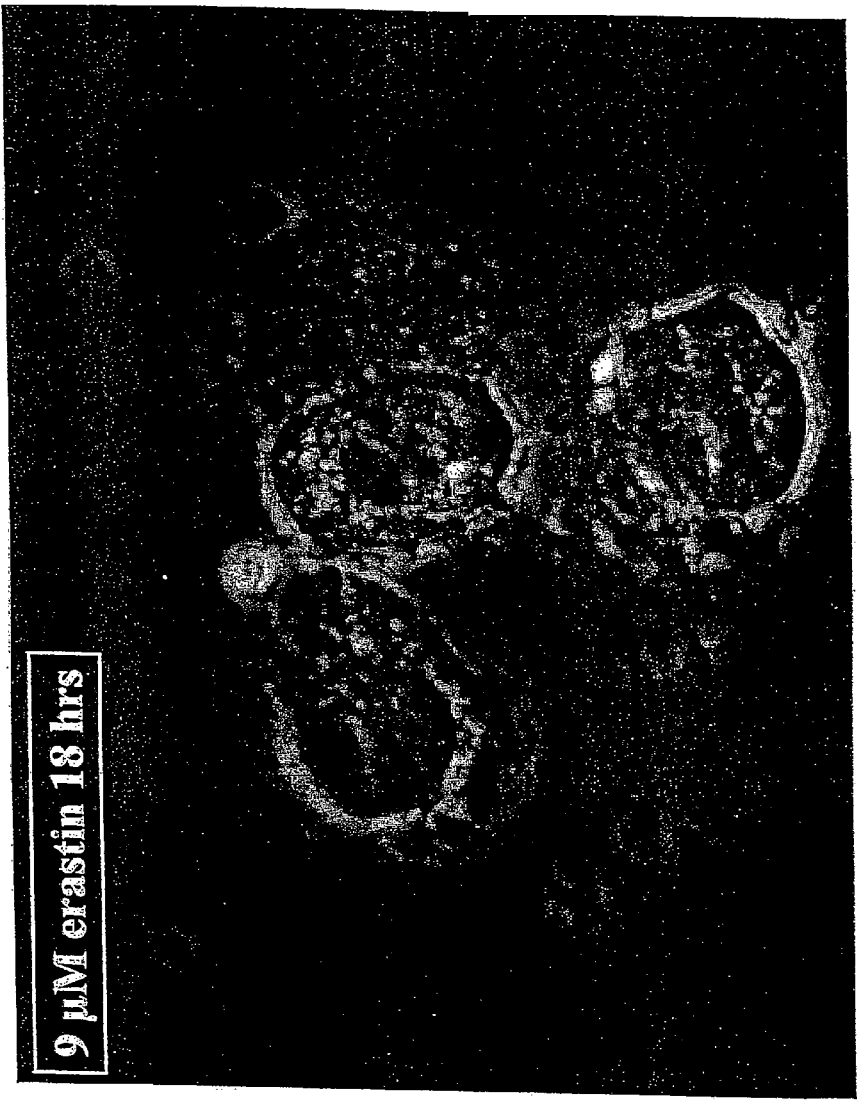
FIG. 9 shows that nuclei remain intact in erastin-treated tumor cells.

Applicants sought to characterize the type of cell death induced by CPT and erastin in tumorigenic BJ-TERT/LT/ST/$RAS^{V12}$ cells. In other contexts, CPT has been found to induce apoptotic cell death (Traganos et al., 1996, Ann N Y Acad Sci 803, 101-10), which is characterized by alterations in nuclear morphology including pyknosis, karyorhexis and/or margination of chromatin (Majno and Joris, 1995, Am J Pathol 146, 3-15). To determine whether erastin or CPT induces apoptosis in their system, Applicants monitored the nuclear morphology of CPT- and erastin-treated tumorigenic cells using fluorescence microscopy. Although karyorhexis and margination of chromatin were clearly visible in CPT-treated cells, no such morphological alternation was visible in erastin-treated cells (FIG. 7A). Since nuclear morphological change is required of apoptotic cells, Applicants conclude that cell death induced by erastin is non-apoptotic. Further supporting this conclusion were observations that CPT, but not erastin, induces DNA fragmentation (which is formation of a DNA ladder), that a pan-caspase inhibitor (50 µM Boc-Asp(Ome)-fluoromethyl ketone, Sigma #B2682 (Chan et al., 2001, Neuroreport 12, 541-545)), partially blocked cell death induced by CPT, but not by erastin, and that CPT, but not erastin, caused an increase in Annexin V staining (FIG. 7B) and the appearance of cleaved, active caspase 3 (FIG. 7C). Additionally, nuclei remained intact in erastin-treated tumor cells (FIG. 9).

Figure 6:
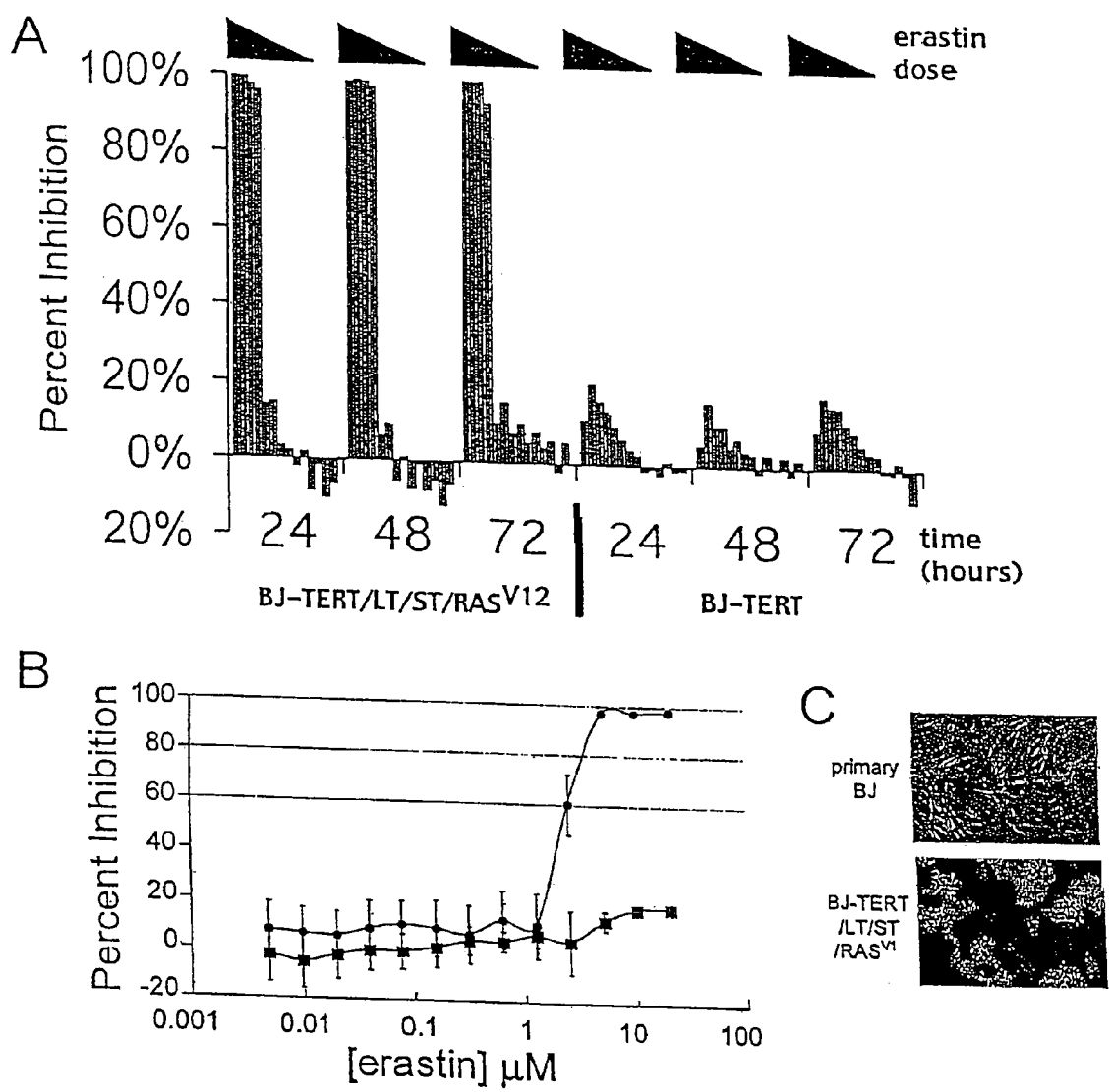
FIGS. 6A-6C show that erastin induces rapid cell death in a ST/RAS$^{V12}$-dependent fashion. (A) Time-dependent effect of erastin on BJ-TERT and BJ-TERT/LT/ST/RAS$^{V12}$ cells. Cells were seeded in 384-well plates in the presence of the indicated concentrations of erastin. Inhibition of cell viability was determined after 24, 48 and 72 hours using calcein AM. (B) Effect of erastin on Alamar Blue viability staining in BJ-TERT (red) and BJ-TERT/LT/ST/RAS$^{V12}$ (blue) cells. (C) Photograph of BJ-TERT/LT/ST/RAS$^{V12}$ and BJ primary cells treated with erastin. Cells were allowed to attach overnight, then treated with 9 μM erastin for 24 hours and photographed.

Erastin's ability to induce non-apoptotic cell death is selective for ST- and $RAS^{V12}$-expressing cells. Longer treatments and higher concentrations of erastin had little effect on the viability of cells lacking $RAS^{V12}$ and ST, confirming the qualitative nature of erastin's selectivity (FIGS. 6A,C). As erastin-treated cells do not undergo apoptosis, Applicants sought to confirm that erastin genuinely induces cell death, rather than cell detachment. They quantitated cell viability in the presence of erastin using Alamar Blue (Ahmed et al., 1994, J. Immunol. Methods 170, 211-224), a viability dye that measures intracellular reductive potential. Erastin exhibited selective lethality in tumorigenic BJ-TERT/LT/ST/$RAS^{V12}$ cells relative to BJ-TERT cells in this homogeneous Alamar Blue viability assay (FIG. 6B). BJ-TERT/LT/ST/$RAS^{V12}$ cells treated with erastin for 18 hours rounded up and detached (FIG. 6C), failed to exclude the vital dye Trypan Blue, displayed a loss of mitochondrial membrane potential as assayed by the potentiometric dye JC-1, and had a small cell size characteristic of dead cells. Applicants determined that the loss of viability induced by erastin is irreversible once completed, in that BJ-TERT/LT/ST/$RAS^{V12}$ cells treated with erastin for 24 hours rounded up, detached and were unable to recover when replated in erastin-free medium. Thus, erastin induces rapid (12-24 h), irreversible, non-apoptotic cell death in a ST- and $RAS^{V12}$-dependent fashion.

Figure 10:
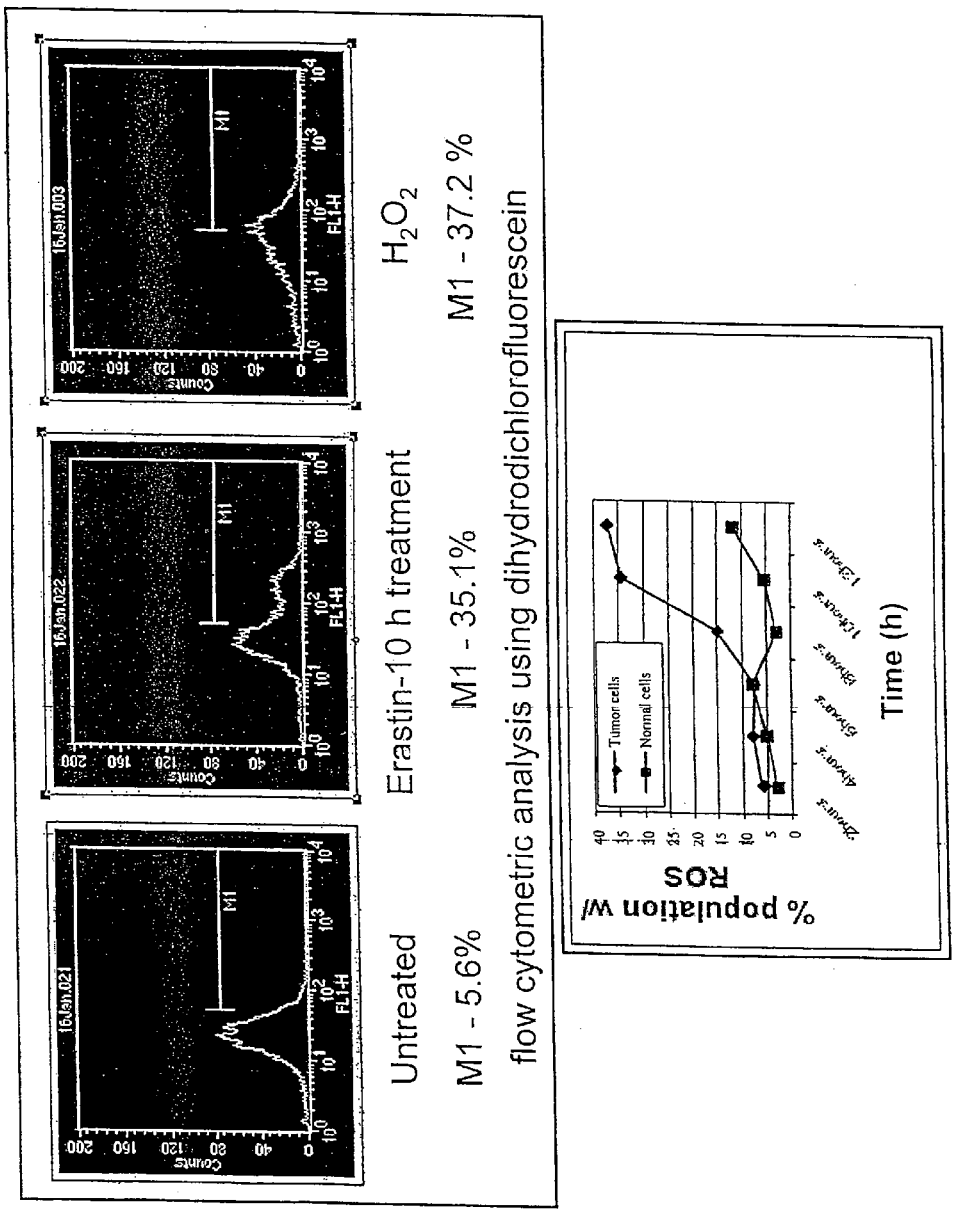
FIG. 10 shows that erastin induces the formation of reactive oxygen species.

Studies were additionally conducted that demonstrated that erastin induces the formation of reactive oxygen species (see FIG. 10).

Screens for suppressors (inhibitors) of erastin activity were carried out. Four anti-oxidants that suppress erastin activity were identified, one of which was the anti-oxidant, α-tocopherol.

The following methods and materials were used in the examples described herein.

Constructs and Retroviruses

Expression constructs for hTERT, LT, ST, SV40 Early Region, and $HRAS^{V12}$ were used as previously described (Hahn et al., 1999, supra; Hahn et al., 2002, supra)). hTERT-pWZL-Blastε, E6-pWZL-zeoε, and E6E7-pWZL-Zeoε were previously described (Lessnick et al., 2002, supra). The E6 and LT cDNAs were cloned into the pWZL-Hygroε retroviral vector (a kind gift from J. Morgenstern, Millenium Pharmaceuticals). Vesicular stomatitis virus-G glycoprotein pseudotyped retroviruses were prepared, and infections carried out as described previously (Lessnick et al., 2002, supra).

Cell Lines

TIP5 primary fibroblasts (Lessnick et al., 2002, supra) were prepared from discarded neonatal foreskins and were immortalized by infection with hTERT-pWZL-blastε or hTERT-pBabe-hygro retroviruses and selection with either blasticidin or hygromycin, respectively. BJ cells were a gift of Jim Smith. hTERT-immortalized fibroblasts were infected with the indicated retroviruses and selected for the appropriate markers. All BJ derivatives were cultured in a 1:1 mixture of DMEM and M199 supplemented with 15% inactivated fetal bovine serum, penicillin and streptomycin (pen/strep). TIP5 cells were grown in DMEM containing 10% FBS and pen/strep. All cell cultures were incubated at 37° C. in a humidified incubator containing 5% $CO_2$.

Compound Libraries

An annotated compound library (ACL) comprising 1,540 compounds, an NCI diversity set of 1,990 compounds obtained from the National Cancer Institute and a combinatorial library (Comgenex International, Inc.) containing 20,000 compounds were used in the tumor-selective synthetic lethal screens. All compound libraries were prepared as 4 mg/ml solutions in DMSO in 384-well polypropylene plates (columns 3-22) and stored at −20° C. Camptothecin (cat# C9911, MW 348.4), doxorubicin (cat# D1515 MW 580.0), daunorubicin (cat# D8809, MW 564.0), mitoxantrone (cat# M6545, MW 517.4), okadaic acid (cat# 04511, MW 805.0), echinomycin (cat# E4392, MW 1101), sangivamycin (cat# S5895, MW 309.3) were obtained from Sigma-Aldrich Co. Bouvardin (MW 772.84) and NSC146109 (MW 280.39) were obtained from the National Cancer Institute's Developmental Therapeutics Program. Erastin (MW 545.07) was obtained from Comgenex International, Inc.

Calcein AM Viability Assay

Calcein acetoxylmethyl ester (AM) is a cell membrane-permeable, non-fluorescent compound that is cleaved by intracellular esterases to form the anionic, cell-impermeable, fluorescent compound calcein. Viable cells are stained by calcein because of the presence of intracellular esterases and because the intact plasma membrane prevents fluorescent calcein from leaking out of cells (Wang et al., 1993, supra). Cells were seeded in 384-well plates using a Zymark Sciclone ALH, treated with each compound in triplicate at 4 µg/mL in the primary screen for two days, washed with phosphate-buffered saline on a Packard Minitrak with a 384-well washer and incubated for four hours with 0.7 µg/mL calcein (Molecular Probes). Total fluorescence intensity in each well was recorded on a Packard Fusion platereader, and converted to a percent inhibition of signal by subtracting the instrument background and dividing by the average signal obtained when cells were not treated with any compound.

Alamar Blue Viability Assay

Alamar Blue is reduced by mitochondrial enzyme activity in viable cells, causing both colorimetric and fluorescent changes (Nociari et al., 1998, J. Immunol. Methods 13, 157-167). Cells were seeded at a density of 6000 cells (50 µl) per well in a 384-well black, clear bottom plate using a syringe bulk dispenser (Zymark). 10 µl was removed from a two-fold serially diluted erastin plate (6× final concentration) using a 384 fixed cannula head, making the final concentration 20 µg/ml in the well with highest concentration. The plates were incubated for 24 hours. Alamar Blue (Biosource International) was added to each well by diluting 1:10 and incubated for 16 hours at 37° C. Fluorescence intensity was determined using a Packard Fusion platereader with an excitation filter centered on 535 nm and an emission filter centered on 590 nm. Average percentage inhibition at each concentration was calculated. Error bars indicate one standard deviation. The Alamar Blue assay does not involve washing the cells.

Screening

Replica daughter plates were prepared with a Zymark Sciclone ALH and integrated Twister II by diluting stock plates 50 fold in medium lacking serum and pen/strep to obtain a compound concentration in daughter plates of 80 µg/ml with 2% DMSO. Assay plates were prepared by seeding cells in black, clear bottom 384-well plates in columns 1-23 (6000 cells/well in 57 µl) using a syringe bulk dispenser. Columns 3-22 were treated with compounds from a daughter library plate by transferring 3 µl from the daughter library plate using 384-position fixed cannula array. The final compound concentrations in assay plates were thus 4 µg/ml. The assay plates were incubated for 48 hours at 37° C. in humidified incubator containing 5% $CO_2$. Plate processing for the calcein AM viability assay was performed using an integrated Minitrak/Sidetrak robotic system from Packard Bioscience (Perkin Elmer). Assay plates were washed with phosphate buffered saline, and 20 µl of calcein AM (0.7 µg/ml) per well was added. Plates were incubated at room temperature for 4 hours. Fluorescence intensity was determined using a Fusion platereader with filters centered on an excitation of 485 nm and an emission of 535 nm.

Retesting of Compounds in a Dilution Series

Compounds to be retested were purchased from manufacturers. Stocks were prepared in DMSO at a concentration of 1 mg/ml in 384-well polypropylene plates with a 16-point, two-fold dilution dose curve of each compound in a column, in duplicates. Column 1-2 and 23-24 were left empty for controls. Daughter retest plates were prepared from stock retest plate by diluting 66.6 fold in DMEM in 384-well deep-deep well plates (4.5 µl transfer into 300 µl). Cells were seeded at a density of 6000 per well in 40 µl, and 20 µl was added from a daughter retest plate. The plates were incubated for two days at 37° C. with 5% $CO_2$.

Data Analysis

Mean RFU (relative fluorescence units) for untreated cells was calculated by averaging columns 1, 2, and 23 (wells with cells but lacking compounds). The calcein background was calculated by averaging column 24 (wells with calcein, but lacking cells). Percentage inhibition of each well was calculated as [1−(RFU−calcein control)/(untreated cell−calcein control)*100]. Compounds causing at least 50% inhibition of calcein staining in the primary screen were tested for selectivity towards BJ-TERT/LT/ST/RAS$^{V12}$ engineered tumor cells by testing in BJ primary and BJ-TERT/LT/ST/RAS$^{V12}$ cells at a range of concentrations. Selective compounds were retested in all engineered cell lines.

Nuclear Morphology Assay 200,000 tumorigenic BJ-TERT/LT/ST/RAS$^{V12}$ cells were seeded in 2 mL on glass coverslips in each well of a six-well dish, treated with nothing (NT), 9 µM erastin or 1.1 µM camptothecin (CPT) in growth medium for 18 hours while incubating at 37° C. with 5% $CO_2$. Nuclei were stained with 25 µg/mL Hoechst 33342 (Molecular Probes) and viewed using an oil immersion 100× objective on a fluorescence microscope.

Cell Size Measurements 200,000 BJ-TERT/LT/ST/RAS$^{V12}$ cells were seeded in six-well dishes in 2 mL growth medium only (No treatment), with 9 µM erastin or with 1.1 µM camptothecin (CPT). After 24 hours, cells were released with trypsin/EDTA, diluted to 10 mL in growth medium, and the cell size distribution of each sample was determined on a Coulter Counter.

Cell Counting Assay for Camptothecin Activity

BJ-TERT/LT/ST/RAS$^{V12}$ cells were seeded in 6-well dishes (200 000 cells/well; 2 ml per well) and transfected in serum- and antibiotic-free medium using Oligofectamine (Life Technologies), with 100 nM siRNA per well in a total volume of one milliliter. 500 μl of medium containing 30% FBS was added 4 hours after transfection. Cells were treated with the indicated concentrations of camptothecin 30 hours after transfection. 500 μl of a 5× solution of the desired camptothecin concentration was added to each well. Cells were removed with trypsin-EDTA and counted using a hemacytometer 75 hours after transfection. Control experiments indicated the transfection efficiency was approximately 10%.

Western Blot Analysis

Caspase-3

BJ-TERT/LT/ST/RAS$^{V12}$ cells were seeded prior to the experiment at $5 \times 10^5$ cells in 60 mm dishes. The cells were treated with 5 μg/ml erastin (9 μM) for 2, 4, 6, 8 or 10 hours. One dish was maintained for camptothecin treatment (0.4 μg/ml for 24 h) as a positive control. Cells were lysed after each time point in lysis buffer (50 mM HEPES KOH pH 7.4, 40 nM NaCl, 2 mM EDTA, 0.5% Triton X-100, 1.5 mM $Na_3VO_4$, 50 mM NaF, 10 mM sodium pyrophosphate, 10 mM sodium beta-glycerophosphate and protease inhibitor tablet (Roche)). Protein content was quantified using a Biorad protein assay reagent. Equal amounts of protein were resolved on 16% SDS-polyacrylamide gel. The electrophoresed proteins were transblotted onto a PVDF membrane, blocked with 5% milk and incubated with anti-active caspase-3 polyclonal antibody (BD Pharmingen) at 1:1500 dilution overnight at 4° C. The membrane was then incubated in anti-rabbit-HRP (Santa Cruz Biotechnology) at 1:3000 dilution for 1 hour and developed with an enhanced chemiluminescence mixture (NEN life science, Renaissance). To test for equivalent loading in each lane, blots were stripped, blocked, and probed with an anti-eIF-4E antibody (BD Transduction laboratories) at 1:1000 dilution.

Topoisomerase-IIα

BJ, BJ-TERT, BJ-TERT/LT/ST, BJ-TERT/LT/ST/RAS$^{V12}$, BJ-TERT/LT/RAS$^{V12}$ and BJ-TERT/LT/RAS$^{V12}$/ST cells were seeded at $1 \times 10^6$ cells per dish in 60 mm dishes. After overnight incubation of the cells at 37° C. with 5% $CO_2$, the cells were lysed as described above and proteins resolved on a 10% polyacrylamide gel. The membrane was incubated with monoclonal anti-human topoisomerase IIα p 170 antibody (TopoGEN) at 1:1000 dilution overnight at 4° C. and then with anti-mouse HRP (Santa Cruz Biotechnology).

Topoisomerase 1 (TOP1)

A 21-nucleotide double stranded siRNA directed against TOP1 (nucleotides 2233-2255, numbering from the start codon, Genbank accession J03250) was synthesized (Dharmacon, purified and desalted/deprotected) and transfected (100 nM) into and BJ-TERT/LT/ST/RAS$^{V12}$ cells in six-well dishes with oligofectamine (Life Technologies). After 75 hours, cells were lysed and the expression level of TOP1 determined by Western blot (Topogen, Cat# 2012-2, 1:1000 dilution). The protein loading level was determined by stripping and reprobing the same blot with an antibody directed against eIF-4E (BD Biosciences, Cat# 610270, 1:500 dilution). Alternatively, $1 \times 10^6$ cells were seeded in 60 mm dishes and grown overnight at 37° C. with 5% $CO_2$, then lysed with 150 μl of lysis buffer. Cells were removed with a scraper and transferred to microcentrifuge tubes and incubated on ice for 30 minutes. The protein contents in the lysates were quantified using a Biorad protein estimation assay reagent. Equal amounts of protein were loaded on 10% gradient SDS-polyacrylamide gel. The electrophoresed proteins were transblotted onto PVDF membrane. After blocking with 5% dry milk, the membrane was incubated with mouse anti-human topoisomerase I antibody (Pharmingen) overnight at 4° C., then with anti-mouse peroxidase conjugate antibody (Santa Cruz Biotechnology).

Annexin V-FITC Apoptosis Assay

BJ-TERT/LT/ST/RAS$^{V12}$ cells were seeded at $1 \times 10^6$ cells per dish in 100 mm dishes and allowed to grow overnight. Cells were treated with erastin (5 or 10 μg/ml) for 6, 8 or 11 h. A camptothecin-treated (0.4 μg/ml) control was maintained, treated at the time of seeding for 20 hours. After the treatment, cells were harvested with trypsin/EDTA and washed once with fresh medium containing serum and then twice with phosphate buffered saline. Cells were resuspended in 1× binding buffer (BD Pharmingen) at a concentration of $1 \times 10^6$ cells/ml. 100 μl ($1 \times 10^5$ cells) was incubated with 5 μl of Annexin V-FITC (BD Pharmingen) and propidium iodiode (BD Pharmingen) for 15 minutes in the dark at room temperature. Then 400 μl of the 1× binding buffer was added and the cells analyzed by flow cytometry (Becton-Dickinson). Data were acquired and analyzed using Cellquest software. Only viable cells that did not stain with propidium iodiode were analzyed for Annexin V-FITC staining using the FL1 channel.

ROS Analysis: Flow Cytometry Analysis Using H2DCF-DA

2'7' dichlorodihydrofluorescein diacetate (H2DCF-DA) is a non-fluorescent cell permeable compound. The endogenous esterase enzyme inside the cell cleaves the diacetate part, and it can no longer pass out of the cell. Thus it accumulates in the cell. Then H2DCF reacts with ROS to form fluorescent dichlorofluorescene (DCF) which can be measured by flow cytometry in FL1 channel.

1. Seed cells at $3 \times 10^5$ cells per dish in 60 mm dishes and allow to grow overnight.

2. Treat with the test compound for different period of time (1-10 hr).

3. Maintain one dish for untreated cells, compound treated cell and positive control dish (hydrogen peroxide treated) for each time point.

4. Incubate the cells with 10 μM of H2DCF-DA for 10 minutes at 37° C.

5. For positive control cells, after 5 minutes of H2DCF-DA loading, add 500 μM of hydrogen peroxide and incubate for 5 minutes further.

6. Harvest the cell by trypsinization.

7. Wash with cold PBS-twice.

8. Resuspend the pellet in 100 μl of PBS and transfer into 5 ml FACS tube.

9. Add 5 μl of propidium iodide (50 μg/ml) and incubate for 10 minutes on ice in dark.

10. Add 400 μl of PBS and analyze by flow cytometry (Becton-Dickinson).

11. Acquire the data and analyze using CellQuest software program.

12. Take only propidium iodiode negative cells (viable cells) for the analysis for DCF staining using the FL1 channel, PI in FL3 channel, plot a quadrant chart.

Screens of ACL library for compounds that can suppress erastin activity in BJELR cells.

Method:

ACL library comprises 1,540 compounds and all compounds were prepared in DMSO at 4 μg/ml in 384-well polypropylene plates and stored at −20° C. Replica daughter plates for each library plate were prepared using Zymark Scilone ALH. The daughter plates were diluted 50 fold in DMEM and compound concentration in the daughter plate is 80 μg/ml with 2% DMSO. In assay plate compound from the daughter plate is diluted 20 fold with cell suspension, thus final concentration of each compound is 4 μg/ml.

BJELR cells were seeded at 6000 cells/well (57 μl) (for co-treatment screen) and 5000 cells/well (57 μl) (for pretreatment screen) in 384-well black, clear bottom plates using syringe bulk dispenser. For co-treatment suppressor screen, cells were treated with 3 μl of compound from the daughter plates of ACL library (final concentration in assay plate at 4 μg/ml) and at the same time treated with 5 μg/ml of erastin. Compound transfer was done using 384 fixed cannula head. Plates were incubated for 48 hours at 37° C. in incubator with 5% $CO_2$. For the pretreatment screens, cells were pre-incubated with the compound from ACL daughter library plate for overnight and then treated with 5 μg/ml of erastin for further 48 hours. Plates were processed for Calcein assay using MiniTrak/SideTrak robotic system from Packard BioScience. Assay plates were washed with PBS and incubated with Calcein AM (0.7 μg/ml) for 4 hours at room temperature. Fluorescence intensity was determined using Fusion platereader with filters centered in an excitation of 485 nm and emission of 535 nm. BJELR cells are BJ-TERT/LT/ST/$RAS^{v12}$ cells. Table 1. Potencies of tumor-selective compounds in engineered cell lines. Nine tumor-selective compounds were retested in 16-point, two-fold dilution dose-curves in all engineered cell lines. The table lists the concentration (in μg/mL) required to achieve 50% inhibition of calcein AM staining ($IC_{50}$) for each compound in each cell line. The $IC_{50}$ in primary BJ cells was divided by the $IC_{50}$ in BJ-TERT/LT/ST/$RAS^{V12}$ tumorigenic cells to obtain a tumor selectivity ratio for each compound. The compound selectivity for each genetic element was determined by calculating the selectivity ratio for each subsequent pair of cell lines in a series. Small T oncoprotein-selective compounds were considered to be selective for PP2A (the target of small T oncoprotein), whereas E6-selective compounds were considered to be selective for loss of p53 and E7-selective compounds were considered to be selective for loss of RB.

| | BJ | BJ-TERT | BJ-TERT/LT/ST | BJ-TERT/LT/ST/$Ras^{v12}$ | BJ-TERT/LT/$Ras^{v12}$ | BJ-TERT/LT/$Ras^{v12}$/ST | BJ-TERT/p53OD/$CDK4^{R24C}$/cyclinD1/ST/$Ras^{v12}$ | TIP5-TERT | TIP5-TERT/LT | TIP5-TERT/LT/ST | TIP5-TERT/LT/ST/$Ras^{v12}$ |
|---|---|---|---|---|---|---|---|---|---|---|---|
| Echinomycin | >5 | 0.312 | 0.0048 | 0.0012 | 0.0048 | 0.0012 | 0.078 | >5 | 5 | 0.0048 | 0.0024 |
| Sangivamycin | 0.312 | 0.039 | 0.195 | 0.078 | 0.078 | 0.078 | 0.078 | 1.25 | 0.312 | 0.039 | 0.078 |
| NSC146109 | >5 | 5 | 2.5 | 2.5 | 5 | 2.5 | 5 | >5 | >5 | 5 | 2.5 |
| Bouvardin | 0.312 | 0.078 | 0.0195 | 0.078 | 0.078 | 0.0195 | 0.156 | >5 | 0.312 | 0.039 | 0.039 |
| Mitoxantrone | 5 | 1.25 | 0.312 | 0.312 | 1.25 | 0.312 | 1.25 | >5 | 1.25 | 0.625 | 1.25 |
| Doxorubicin | >5 | 1.25 | 0.312 | 1.25 | 1.25 | 1.25 | 1.25 | >5 | 1.25 | 0.625 | 0.625 |
| Daunorubicin | 5 | 1.25 | 0.312 | 0.312 | 1.25 | 0.625 | 0.625 | >5 | 1.25 | 0.625 | 0.625 |
| Camptothecin | >5 | >5 | 1.25 | 0.0195 | 1.25 | 0.0195 | 1.25 | >5 | >5 | 0.156 | 0.156 |
| Erastin | >5 | >5 | >5 | 1.25 | >5 | 1.25 | 2.5 | >5 | >5 | 5 | 2.5 |

| | TIP-TERT/E6 | TIP5-TERT/E6E7 | TIP5-TERT/E6E7/ST | TIP5-TERT/E6E7/ST/$Ras^{v12}$ | Tumor Selectivity | Genetic basis of Selectivity |
|---|---|---|---|---|---|---|
| Echinomycin | >5 | 0.048 | 0.048 | 0.0048 | >8333 | non-specific |
| Sangivamycin | 0.156 | 0.078 | 0.078 | 0.078 | 4 | non-specific |
| NSC146109 | 5 | 2.5 | 2.5 | 2.5 | >4 | non-specific |
| Bouvardin | 0.078 | 0.039 | 0.039 | 0.078 | 4 | non-specific |
| Mitoxantrone | 1.25 | 0.625 | 0.625 | 1.25 | 16 | TERT/RB |
| Doxorubicin | 5 | 1.25 | 1.25 | 1.25 | >8 | TERT/RB |
| Daunorubicin | 5 | 0.625 | 0.625 | 0.625 | 16 | TERT/RB |
| Camptothecin | >5 | 0.625 | 0.156 | 0.156 | >512 | $RAS^{v12}$/PP2A/RB |
| Erastin | >5 | >5 | >5 | 5 | >8 | $RAS^{v12}$/PP2A |

Example 4 Screens for Small Molecule Suppressors of Expanded Huntingtin in Mammalian Cells There are nine inherited neurodegenerative disorders caused by a polyglutamine (polyQ)-encoding trinucleotide (CAG) repeat expansion within the coding sequence of a gene (Zoghbi H Y and Orr H T, Annu Rev Neurosci 2000, 23: 217-47; Nakamura K, et al., Hum Mol Genet 2001, 10: 1441-8). These diseases include Huntington's Disease (The Huntington's disease collaborative research group, Cell 1993, 72: 971-83), spinobulbar muscular atrophy (La Spada A R, et al., Nature 1991, 352: 77-9), dentatorubral pallidol-uysian atrophy (Koide R, et al., Nat Genet 1994, 6: 9-13; Nagafuchi S, et al., Nat Genet 1994, 6: 14-8), and the spinocerebellar ataxias type 1, 2, 3, 6, 7, and 17 (Nakamura K, et al., Hum Mol Genet 2001, 10: 1441-8; Orr H T, et al., Nat Genet 1993, 4: 221-6; Kawaguchi Y, et al., Nat Genet 1994, 8: 221-8; Imbert G, et al., Nat Genet 1996, 14: 285-91; Pulst S M, et al., Nat Genet 1996, 14: 269-76; Sanpei K, et al., Nat Genet 1996, 14: 277-84; David G, et al., Nat Genet 1997, 17: 65-70; Koob M D, et al., Nat Genet 1998, 18: 72-5). Although the length of the CAG expansion is variable in these disorders, the threshold for toxicity is approximately 40 CAG repeats, with longer repeat lengths generally resulting in earlier disease onset (Gusella J F & MacDonald M E, Nat Rev Neurosci 2000, 1: 109-15). Precisely how polyQ mutations lead to neuronal loss in each disease remains unclear; however, several molecular characteristics appear to be shared among the different disorders. Such characteristics include deficiencies in ubiquitin-mediated proteolysis, protease-dependent accumulation of polyQ protein fragments, formation of cytosolic and nuclear inclusions, and changes in gene expression (Zoghbi H Y and Orr H T, Annu Rev Neurosci 2000, 23: 217-47; Kaytor M D & Warren S T, J Biol Chem 1999, 274: 37507-10; Orr H T, Genes Dev 2001, 15: 925-32; Taylor J P, et al., Science 2002, 296: 1991-5; Rubinsztein D C, Trends Genet 2002, 18: 202-9).

The slow, progressive characteristic of Huntington's Disease (HD) makes it difficult to study in humans, although postmortem brain analysis of HD patients has been useful in revealing extensive neuronal loss in regions of the brain functionally affected during the course of the disease (Gutekunst C A, et al., J Neurosci 1999, 19: 2522-34). Although the huntingtin protein is expressed in many cell types, there is a relatively selective disappearance of medium spiny neurons in the striatum of patients with HD. Cell-based models that recapitulate aspects of this cell-type specific death are of value (Schweitzer E S, et al., submitted).

Applicants have developed two high-throughput, neuronal cell-based screens related to Huntington's Disease. Both assays exhibit mutant huntingtin-dependent toxicity that is found selectively in neuronal cells. These screens allowed us to identify small molecules that prevent the toxicity of the expanded, polyglutamine-containing huntingtin protein in neuron-like cells in culture.

Figure 11:
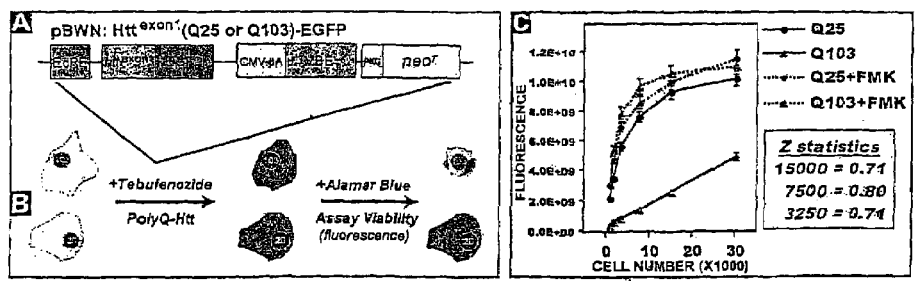
FIG. 11 shows modeling Htt-polyQ neurotoxicity in PC12 cells. (A) Inducible construct for production of Htt-EGFP fusion proteins. Rat neuronal PC12 cells are transfected with Htt-exon-1 constructs containing either 25 (Q25) or 103 (Q103) polyglutamine repeats (mixed CAG/CAA). (B) Cartoon of Htt-exon-1 expression in PC12 cells and screening assay for cell viability using Alamar Blue. Induction of Htt-Q103 expression leads to the formation of perinuclear cytoplasmic inclusions (or aggresomes) of the fusion protein followed by cytotoxicity after 48 hours. Expression of Htt-Q25 remains diffuse throughout the cytoplasm and is not cytotoxic. (C) Quantification of Htt-Q25 and Htt-Q103 cell viability as a measure of Alamar Blue fluorescence. Note addition of the general caspase inhibitor (BOC-D-FMK, 50 mM) rescues Htt-Q103 toxicity after a 72 hour induction with tebufenozide (Z-statistics calculated for 15000, 7500, and 3250 cells, yellow box).

In the first cell system, Applicants developed, in collaboration with Dr. Erik Schweitzer (UCLA), a high-throughput screen (HTS) for compounds that rescue polyQ-induced apoptosis in immortalized rat neuronal cells (Suhr S T, et al., Proc Natl Acad Sci USA 1998, 95: 7999-8004). PC12 rat pheochromocytoma cells were transfected with exon-1 of the human huntingtin gene containing either 25 or 103 N-terminal polyQ repeats. For enhanced stability the repeat portion consists of alternating CAG/CAA repeats (FIG. 11A). In addition, the expression construct incorporates enhanced green fluorescent protein (EGFP) as a reporter that enables tracking of the fusion proteins by direct immunofluorescence microscopy or biochemical (immunoprecipitation or Western blotting) detection with anti-EGFP antibodies (Schweitzer E S, et al., submitted). Finally, expression is regulated using the *Bombyx mori* ecdysone receptor and ecdysone analog, tebufenozide (Suhr S T, et al., Proc Natl Acad Sci USA 1998, 95: 7999-8004).

Following induction with tebufenozide, these cells express comparable levels of either mutant or non-mutant forms of huntingtin. Mutant huntingtin (Q103)-expressing, but not wild-type huntingtin (Q25)-expressing, cells display perinuclear cytoplasmic inclusions (CIs) and begin to die 24 hours after induction of expression (FIG. 11C). Expression of the Q103 construct in an astrocyte-like cell line (BAS 8.1) did not result in perinuclear aggesome formation or cytotoxicity, demonstrating that toxicity of Htt in this model is cell-type-specific.

In the second cell system, Applicants developed a high-throughput screen in collaboration with Elena Cattaneo (University of Milano, Italy) using embryonic rat striatal neuronal cells immortalized with a temperature-sensitive SV40 Large T antigen (ST14A cells). These ST14A cells have been engineered to express constitutively either an N-terminal 548 amino acid fragment of the human huntingtin protein (wt) or the pathogenic version containing an expanded polyglutamine (mutant). Both of these cell lines proliferate normally at the permissive temperature (33° C.) but upon a shift to the non-permissive temperature (39° C.), T antigen is degraded and the cells differentiate into striatal neuronal cells (Ehrlich M E, et al., Exp Neurol 2001, 167: 215-26; Rigamonti D, et al., J Neurosci 2000, 20: 3705-13; Weinelt S, et al., J Neurosci Res 2003, 71: 228-36; Torchiana E, et al., Neuroreport 1998, 9: 3823-7; Cattaneo E & Conti L, J Neurosci Res 1998, 53: 223-34; Cattaneo E, et al., J Biol Chem 1996, 271: 23374-9; Corti O, et al., Neuroreport 1996, 7: 1655-9). These differentiated cells are sensitive to the toxic effects of mutant huntingtin and die at an enhanced rate compared to the wt huntingtin-expressing cells.

1. PC 12 Assay System

Assay Development

The high-throughput screen developed by Applicants using the PC12 cell system uses the fluorescent viability dye Alamar Blue™ (FIG. 11B). Using this assay, Applicants were able to detect up to a five-fold decrease in viability of the Htt-Q103 cells compared to the control Htt-Q25 cells (FIG. 11C). One important parameter in cell-based HTS to be optimized is the cell number per well that yields the best separation between the positive and negative signal (in this case, viable versus dead cells). The Z-factor is a commonly used quantitative index for maximal signal separation and minimal variability. A Z-factor greater than 0.2 is typically required for robust screening results (the theoretical range is from $-\infty$ to 1, with 1 being maximal) (Zhang J H, et al., J Biomol Screen 1999, 4: 67-73). A plot of the mean (N=8) fluorescence (viability) versus a variety of cell numbers revealed that the maximal statistical separation (Z statistic=0.8) occurred at 7500 cells per well.

Caspase inhibitors have been reported to rescue polyQ-mediated toxicity in several systems, including the one described here (Chen M, et al., Nat Med 2000, 6: 797-801; Kim M, et al., J Neurosci 1999, 19: 964-73; Rigamonti D, et al., J Biol Chem 2001, 276: 14545-8; Wellington C L & Hayden M R, Clin Genet 2000, 57: 1-10; Ellerby L M, et al., J Neurochem 1999, 72: 185-95). As a control, Applicants tested the ability of the general caspase inhibitor BOC-D-FMK to rescue Htt-Q103-mediated cell death in this assay system. The addition of 50 µM BOC-D-FMK to Htt-Q103 cells at the time of tebufenozide induction resulted in a complete (100+%) rescue of the Htt-Q103-induced cytotoxicity (FIG. 11C).

Primary Screening

Figure 12:
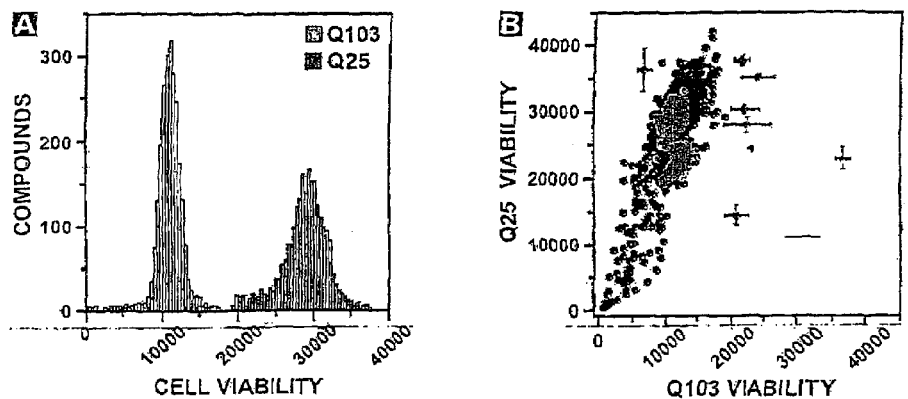
FIG. 12 shows the primary screening of 2500 compounds using the Q25-Htt-exon-1 and Q103-Htt-exon-1 PC12 cell lines. The above plots show two representations of this data set. (A) Histogram plot showing cell viability of Q25-Htt and Q103-Htt expressing PC12 cells after 72 hours in culture with compounds (binning interval is 400 fluorescent units). Cell viability, represented along the horizontal axis, was quantified by Alamar Blue fluorescence. (B) Scatter plot showing cell viability (Q25 versus Q103) following the 72 hour incubation in the presence of each compound (4 μg/ml). Color legend as follows: Black=compounds having either no effect, cytotoxic effect, or slight rescue of cell viability; Red=top 5 compounds that rescued Q103-induced cell death; Blue=one compound that specifically enhanced Q103-mediated cytotoxicity; Green=overlay scatter of 400 control wells without compound (average standard deviation of control wells: Q25=3845, Q103=517). Each data point in plot (B) was calculated from an average of three replicates. The standard deviations (error bars) are shown for the 7 highlighted compounds.

Having defined HTS parameters for the PC12 cell system, Applicants screened approximately 2,500 biologically active compounds from a collection that Applicants had assembled previously. The primary screen of these compounds was performed in triplicate at a concentration of 4 µg/ml (~10 µM) with 0.1% dimethyl sulfoxide. Our procedure for library screening of the PC12 cells consisted of the following: (1) seed cells into 384-well plates with complete medium containing inducing compound (e.g. tebufenozide); (2) transfer library compounds from freshly generated daughter plates to cell culture plates with an integrated Zymark Sciclone/Twister II robot; (3) incubate culture plates for 72 hours (37° C., 9.5% $CO_2$ for PC12 cells); and (4) add viability dye (Alamar Blue™), incubate for an additional 12-16 hours, and read plates in a fluorescence plate reader (Packard integrated minitrak/sidetrak/Fusion). Dilution and detection of Alamar Blue™ was performed as recommended by the manufacture (Biosource International). The results of the primary screen of this library are shown in FIG. 12. This screen revealed several compounds that specifically suppressed Q103-induced toxicity and one compound that operates as an enhancer. These six selective suppressors (FIG. 12B) are not known to function as general death suppressing agents (e.g., as caspase inhibitors).

Secondary Screening

Compounds selected as being drawn from a distribution different from that of the vehicle-treated cells in the primary screen (p<0.05) were retested in an 11-point, two-fold dilution series in four replicates to confirm activity and to determine the dose response. The dilution curves were created robotically using custom-generated software for the Sciclone and Twister II. All other assay conditions for the secondary screen were identical to that of the primary screen with the exception of compound concentration.

2. ST14A Assay System

Assay Development

Applicants used a fluorescence viability assay to monitor cell death in ST14A-Htt$^{wt}$ and ST14A-Htt$^{mut}$ cell lines. The assay is based on conversion of a non-fluorescent substrate (calcein AM, Molecular Probes, Eugene, Oreg.) to a fluorescent product by nonspecific esterases in live cells. Thus, cell death is indicated by a decrease in fluorescence. Cells were seeded in 384-well plates in DMEM medium with 0.1 mM sodium pyruvate and 2 mM glutamine with different amounts of serum. The plates were incubated at 33° C. for 3 h and then shifted to 39° C. (with 5% $CO_2$) and incubated for various time intervals (see below). The wells were washed in phosphate buffered saline ten times, incubated with calcein AM for 4 h and fluorescence was recorded with a read time of 0.2 seconds per well on a fluorescence platereader (Packard Fusion).

Figure 13:
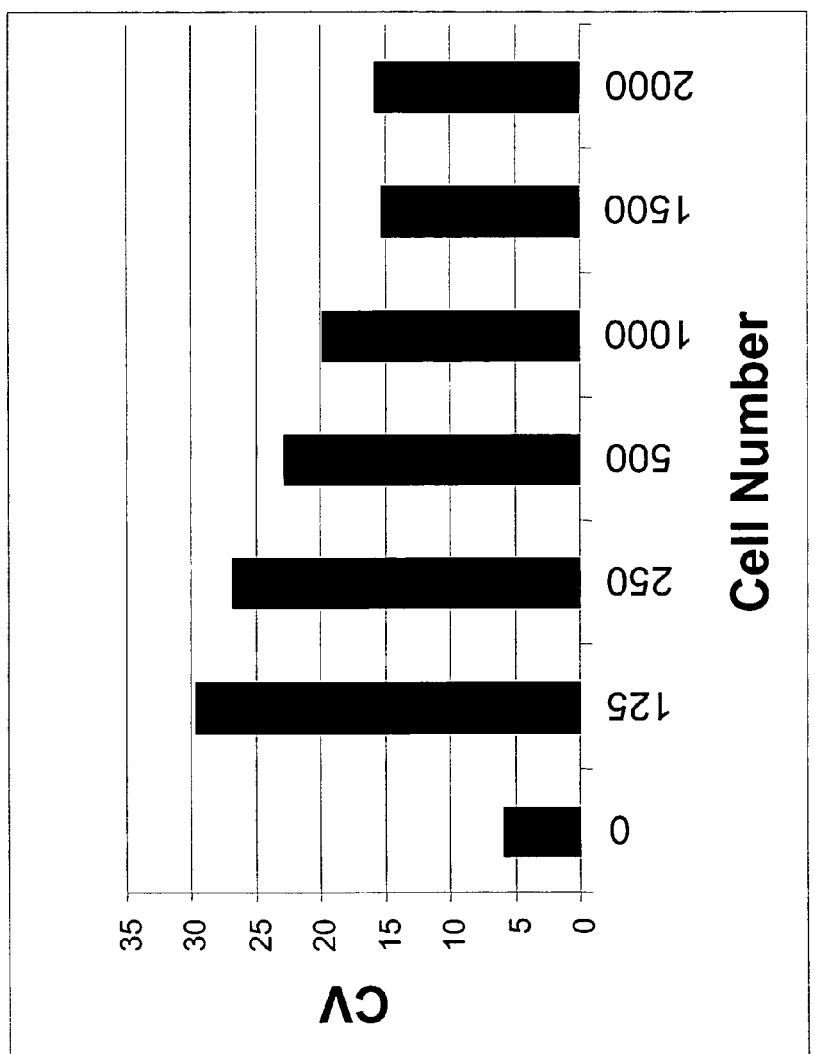
FIG. 13 shows effect of cell density on coefficient of variation (CV).

Applicants tested the range of cell numbers that gave a linear increase in fluorescence. The signal was linear over a range of 125-1500 cells per well and was saturated above 2000 cells per well. The coefficient of variation as a percentage of signal (% CV) was high (30-40%) at low cell density and decreased to 15-20% with 1500 or more cells per well (FIG. 13). The duration of calcein incubation was four hours, as the signal did not saturate with up to five hours of incubation of cells with calcein AM at room temperature. The percentage of serum was titrated to 0.5% inactivated fetal calf serum (Sigma) to enhance cell death such that the average fluorescence of live cells on the day of plating was 2-3 fold higher than cells after three days at 39° C. in 0.5% serum. The Z factor was consistently between 0.1 and 0.25 under these conditions. Although the Z factor is marginal in this assay, Applicants have found it to be sufficient when triplicate measurements are used, as is our standard practice.

Using the optimized assay, Applicants screened our 2,500 bioactive compound library for inhibitors of mutant huntingtin-induced death of ST14A cells. The library was screened twice, with triplicate tests of each compound performed in each screen. The cutoff for a hit was arbitrarily defined as a 1.5-fold increase in signal in comparison to the average fluorescence on the plate in at least two of the three wells of triplicate testing.

Figure 14:
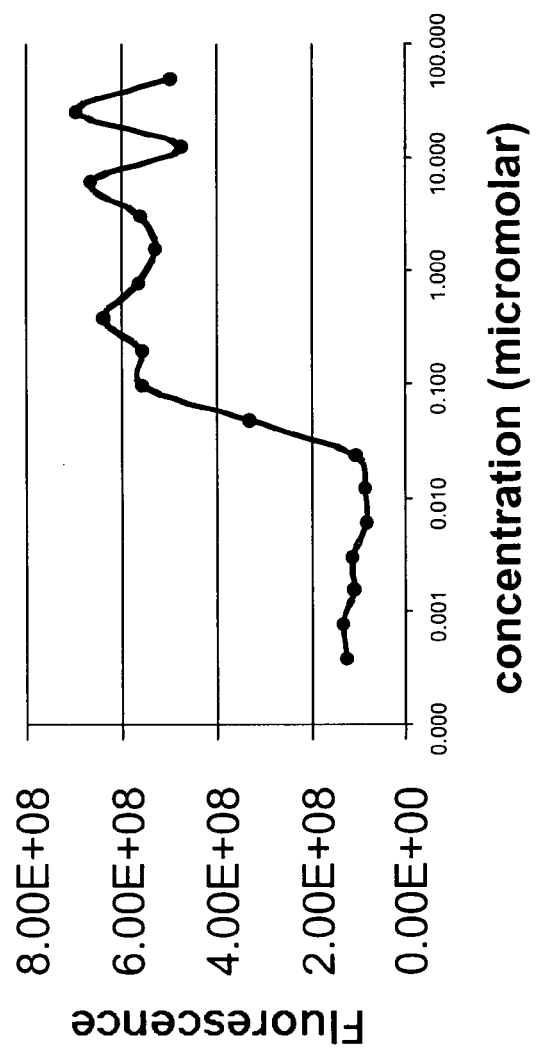
FIG. 14 shows dose response for suppressor of mutant Huntingtin-induced toxicity.

All hits that appeared in the two independent screens of a library were compiled and these potential hits were tested for activity in a dose-titration assay (FIG. 14). Compounds that appeared as positives in the dose-titration assay were reordered from a commercial supplier and were retested again in a dose titration. All compounds that showed activity under these conditions were selected as hits. These compounds were tested for activity in the mutant, wild type and parent cell lines. These selectivity data are indicated in Table 2.

TABLE 2

Selectivity of suppressors in ST14A cell lines

| | Mutant | Wild type | Parent |
|---|---|---|---|
| 1 | + | + | − |
| 2 | + | + | − |
| 3 | + | + | − |
| 4 | + | + | − |
| 5 | + | − | + |
| 6 | + | − | − |
| 7 | + | − | − |
| 8 | + | + | + |
| 9 | + | − | − |
| 10 | + | + | − |
| 11 | + | + | − |
| 12 | + | − | − |

Twelve suppressors of mutant huntingtin-induced death were identified (out of ~2500 tested) in the ST14A cell system. These compounds were tested in six replicates in dilution series in mutant huntingtin-expressing cells, wild-type huntingtin-expressing cells and the parental ST14A cells lacking any construct. Applicants identified four categories of compounds. First, compounds that increase viability of all three cell types. Second, compounds that increase viability of mutant and wild-type huntingtin-expressing cells but not of the parental ST14A cells. Third, compounds that increase viability of both the mutant and parental cells but not the wild-type cells. Fourth, compounds that increase viability only of the mutant cells.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of inducing death in tumor cells, comprising contacting the cells with a compound selected from the group consisting of:

(a) a compound having the following formula:

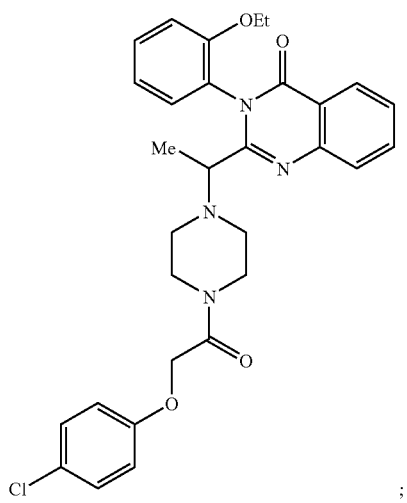

; and (b) a compound having the following formula:

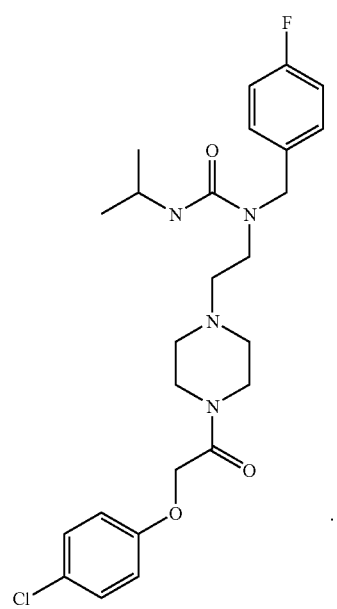

2. A method of inducing death in cells in which the RAS pathway is activated, comprising contacting the cells with a compound selected from the group consisting of:

(a) a compound having the following formula:

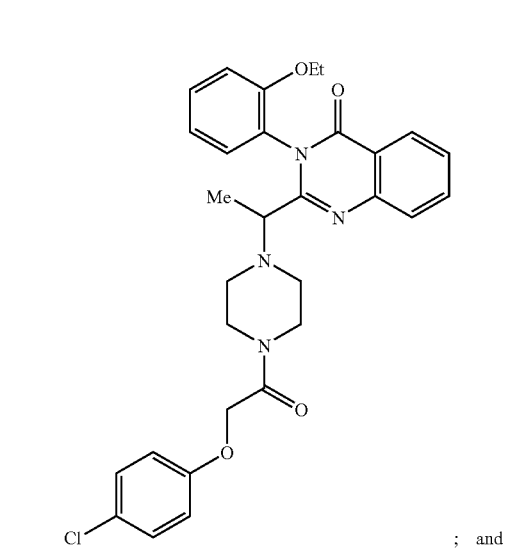

; and (b) a compound having the following formula:

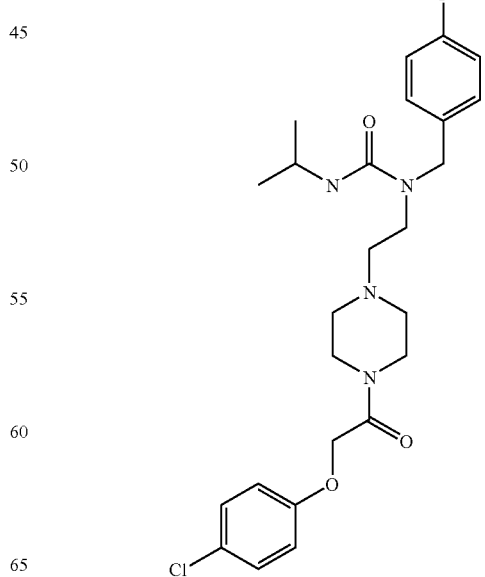

3. A method of inducing death in human cells expressing SV40 small T oncoprotein and oncogenic HRAS, comprising contacting the human cells with a compound selected from the group consisting of:

(a) a compound having the following formula:

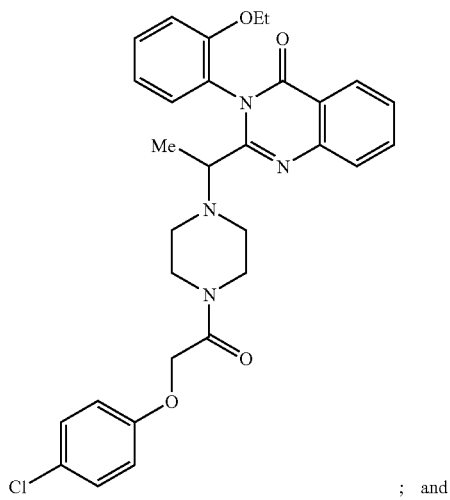

; and (b) a compound having the following formula:

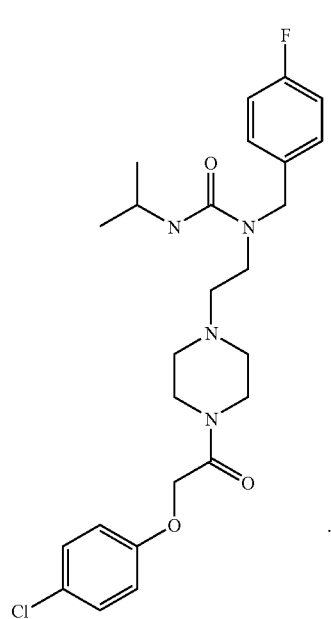

.

4. A pharmaceutical composition comprising a pharmaceutically acceptable carrier and a compound having the following formula:

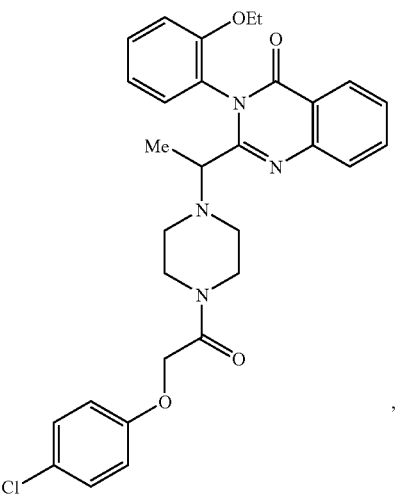

which is selectively toxic to engineered human tumorigenic cells.

5. A pharmaceutical composition comprising a pharmaceutically acceptable carrier and a compound having the following formula:

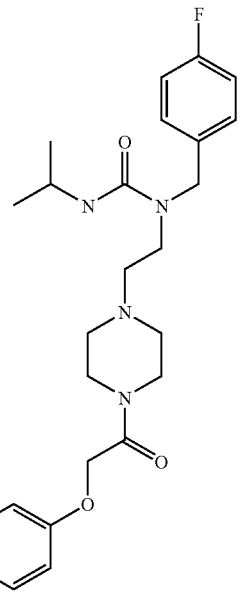

which is selectively toxic to engineered human tumorigenic cells.

* * * * *